US009254245B2

(12) United States Patent
Nieman et al.

(10) Patent No.: US 9,254,245 B2
(45) Date of Patent: Feb. 9, 2016

(54) OPTICALLY GUIDED MEDICAL TUBE AND CONTROL UNIT ASSEMBLY AND METHODS OF USE

(75) Inventors: Timothy R. Nieman, Salt Lake City, UT (US); Trent J. Perry, Kaysville, UT (US)

(73) Assignee: University of Utah, Salt Lake City, UT (US)

( * ) Notice: Subject to any disclaimer, the term of this patent is extended or adjusted under 35 U.S.C. 154(b) by 907 days.

(21) Appl. No.: 13/332,277

(22) Filed: Dec. 20, 2011

(65) Prior Publication Data

US 2012/0116161 A1 May 10, 2012

Related U.S. Application Data

(63) Continuation of application No. 13/332,244, filed on Dec. 20, 2011, now Pat. No. 9,060,922, which is a continuation-in-part of application No. 12/756,129, filed on Apr. 7, 2010, now Pat. No. 8,361,041.

(60) Provisional application No. 61/168,144, filed on Apr. 9, 2009, provisional application No. 61/425,730, filed on Dec. 21, 2010.

(51) Int. Cl.
*A61J 15/00* (2006.01)
*A61B 1/00* (2006.01)
(Continued)

(52) U.S. Cl.
CPC ......... *A61J 15/0046* (2013.01); *A61B 1/00052* (2013.01); *A61B 1/0607* (2013.01);
(Continued)

(58) Field of Classification Search
CPC .......... A61M 25/007; A61M 25/0068; A61M 25/0662; A61M 25/0021; A61B 17/3417; A61B 1/018; A61B 1/12; A61B 1/00135; A61B 1/015; A61B 1/05; A61B 1/042; A61B 1/04; A61B 1/041; A61B 1/0607; A61B 1/2736; A61B 1/07; A61B 1/00052; A61B 1/2733; H04N 2005/2255; A61J 15/0046; A61J 15/0049; A61J 15/0069; A61J 1/07; A61J 15/0007; A61J 15/0073
USPC .......... 604/264, 270; 600/109, 120, 114, 115, 600/116, 139, 146, 156
See application file for complete search history.

(56) References Cited

U.S. PATENT DOCUMENTS 4,253,448 A 3/1981 Terada
4,290,421 A 9/1981 Siegmund
(Continued)

FOREIGN PATENT DOCUMENTS

EP 0400369 12/1990
JP 7-136108 5/1995
(Continued)

OTHER PUBLICATIONS

Preliminary Amendment in U.S. Appl. No. 13/752,150 dated Jan. 28, 2013.
(Continued)

*Primary Examiner* — Manuel Mendez
(74) *Attorney, Agent, or Firm* — Stoel Rives LLP

(57) ABSTRACT

An optical medical tube and control unit assembly and methods of using the same are provided. The optical medical tube may include a steering mechanism and an imaging device which provides the user a visual aid when placing a tube in the body of a patient. The optical medical tube may be coupled to a coupling adaptor to enable quick and easy connecting of the imaging device and steering mechanism of the tube with a control unit such that a single control unit may be used to place multiple feeding tubes or confirm that a feeding tube remains in its proper position without the need for lengthy sterilization procedures between uses.

15 Claims, 36 Drawing Sheets

(51) Int. Cl.

| | |
|---|---|
| ***A61B 1/07*** | (2006.01) |
| ***A61B 1/273*** | (2006.01) |
| ***A61B 1/06*** | (2006.01) |
| *A61M 25/01* | (2006.01) |

(52) U.S. Cl.

CPC ................ *A61B 1/07* (2013.01); *A61B 1/2733* (2013.01); *A61B 1/2736* (2013.01); *A61J 15/0007* (2013.01); *A61J 15/0049* (2013.01); *A61J 15/0069* (2013.01); *A61J 15/0073* (2013.01); *A61J 15/0015* (2013.01); *A61M 25/0147* (2013.01)

(56) References Cited

U.S. PATENT DOCUMENTS 4,315,509 A 2/1982 Smit
4,384,584 A 5/1983 Chen
4,580,551 A 4/1986 Siegmund et al.
4,601,284 A 7/1986 Arakawa et al.
4,615,332 A 10/1986 Buess
4,701,910 A 10/1987 Ulug
4,759,346 A 7/1988 Nakajima
4,769,014 A 9/1988 Russo
4,809,680 A 3/1989 Yabe
4,844,071 A 7/1989 Chen et al.
4,860,731 A 8/1989 Matsuura
4,911,148 A * 3/1990 Sosnowski et al. ........... 600/136
4,998,527 A 3/1991 Meyer
5,085,216 A 2/1992 Henley, Jr. et al.
5,116,317 A 5/1992 Carson, Jr. et al.
5,131,380 A 7/1992 Heller et al.
5,159,446 A 10/1992 Hibino et al.
5,167,220 A 12/1992 Brown
5,441,503 A 8/1995 Considine et al.
5,456,251 A 10/1995 Fiddian-Green
5,571,089 A 11/1996 Crocker
5,577,992 A 11/1996 Chiba et al.
5,630,795 A 5/1997 Kuramoto et al.
5,658,238 A 8/1997 Suzuki et al.
5,665,064 A 9/1997 Bodicky et al.
5,807,314 A 9/1998 Ross et al.
5,855,549 A 1/1999 Newman
5,989,231 A 11/1999 Snow et al.
5,999,678 A 12/1999 Murphy-Chutorian et al.
6,015,400 A 1/2000 Ross et al.
6,030,360 A 2/2000 Biggs
6,322,495 B1 11/2001 Snow et al.
6,322,498 B1 11/2001 Gravenstein et al.
6,447,444 B1 9/2002 Avni et al.
6,461,569 B1 10/2002 Boudreaux
6,464,686 B1 10/2002 O'Hara et al.
6,694,979 B2 2/2004 Deem et al.
6,709,388 B1 3/2004 Mosse et al.
6,712,757 B2 3/2004 Becker
6,802,809 B2 10/2004 Okada
6,994,667 B2 2/2006 Singh
7,169,105 B2 1/2007 Iwasaka et al.
7,220,253 B2 5/2007 Kantsevoy
7,615,002 B2 11/2009 Rothweiler et al.
7,615,003 B2 11/2009 Stefanchik
7,648,457 B2 1/2010 Stefanchik et al.
7,757,695 B2 7/2010 Wilson
2002/0058859 A1 5/2002 Brommersma
2003/0125601 A1 7/2003 Schock et al.
2004/0215061 A1 10/2004 Kimmel et al.
2006/0084838 A1 4/2006 Takuma
2006/0229497 A1 10/2006 Toyama
2006/0258903 A1 11/2006 Stefanchik et al.
2006/0258904 A1 11/2006 Stefanchik et al.
2006/0258907 A1 11/2006 Stefanchik et al.
2006/0258955 A1 11/2006 Hoffman et al.
2006/0259010 A1 11/2006 Stefanchik et al.
2007/0015968 A1 1/2007 Shelnutt
2007/0038027 A1 2/2007 Miyagi et al.
2007/0038031 A1 2/2007 Miyagi et al.
2007/0167683 A1 7/2007 Couvillon
2007/0203393 A1 8/2007 Stefanchik
2007/0260113 A1 11/2007 Otawara
2007/0260119 A1 11/2007 Otawara
2007/0260120 A1 11/2007 Otawara
2007/0270651 A1 11/2007 Gilad
2008/0027408 A1 1/2008 Wilson et al.
2008/0177144 A1 7/2008 Otawara
2008/0208006 A1 8/2008 Farr
2008/0228066 A1 9/2008 Waitzman
2008/0269557 A1 10/2008 Marescaux et al.
2009/0062772 A1 3/2009 Wakeford et al.
2009/0082630 A1 3/2009 Tulley
2009/0275825 A1 11/2009 Thomas
2009/0318757 A1 12/2009 Singh
2009/0318798 A1 12/2009 Singh et al.
2010/0068320 A1 3/2010 Kuwabara
2010/0094116 A1 4/2010 Silverstein

FOREIGN PATENT DOCUMENTS

JP 09-286806 10/1997
WO WO 2005-099376 10/2005
WO WO 2009-108854 9/2009

OTHER PUBLICATIONS

Response to Restriction/Election Requirement in U.S. Appl. No. 13/332,244 dated Apr. 22, 2014.
Restriction/Election Requirement issued in U.S. Appl. No. 13/332,244 on Nov. 22, 2013.
Supplementary European Search Report in PCT/US2010/030429.
Office Action issued in U.S. Appl. No. 12/756,129 on May 9, 2012.
Office Action issued in U.S. Appl. No. 12/756,129 on Oct. 11, 2012.
Notice of Allowance issued in U.S. Appl. No. 12/756,129 on Nov. 13, 2012.
Response to Office Action in U.S. Appl. No. 12/756,129 filed Aug. 2, 2012.
Response to Office Action in U.S. Appl. No. 12/756,129 filed Nov. 2, 2012.
Response to Restriction/Election Requirement in U.S. Appl. No. 12/756,129 filed Feb. 17, 2012.
Restriction/Election Requirement issued in U.S. Appl. No. 12/756,129 on Jan. 18, 2012.
International Search Report from related PCT Patent Application No. PCT/US2011/066324, Jul. 2, 2012.
International Search Report from related PCT Patent Application No. PCT/US2010/030429, Jan. 17, 2011.
Applicant Initiated Interview Summary mailed Sep. 19, 2012 in U.S. Appl. No. 12/756,129.
Applicants Amendment and Response to Office Action filed Jan. 14, 2015 in U.S. Appl. No. 13/332,244.
Applicant's Amendment under 37 C.F.R. §1.312 filed Dec. 13, 2012 in U.S. Appl. No. 12/756,129.
Applicant's Interview Summary, filed Oct. 19, 2012 in U.S. Appl. No. 12/756,129.
Applicant's Preliminary Amendment filed Dec. 20, 2011 in U.S. Appl. No. 13/332,277.
Corrected Notice of Allowance mailed Mar. 30, 2015 in U.S. Appl. No. 13/332,244.
Non-final Office Action mailed Jul. 17, 2014 in U.S. Appl. No. 13/332,244.
Notice of Allowance mailed Feb. 17, 2015 in U.S. Appl. No. 13/332,244.
Response to Rule 312 Communication mailed Dec. 27, 2012 in U.S. Appl. No. 12/756,129.

* cited by examiner 1232
1030
1264
1272
1134
1270
1268
1264
1272
1172
1264
1270
1268
1280
1264

1132
1164
1170
1168
1134
1172
1030
1170
1168
1180

OPTICALLY GUIDED MEDICAL TUBE AND CONTROL UNIT ASSEMBLY AND METHODS OF USE

RELATED APPLICATIONS

The present application is a continuation-in-part of U.S. patent application Ser. No. 12/756,129, filed Apr. 7, 2010, which is expressly incorporated herein by reference and which claims the benefit of U.S. Provisional Patent Application No. 61/168,144, filed Apr. 9, 2009, which is expressly incorporated herein by reference. The present application also claims the benefit of U.S. Provisional Patent Application No. 61/425,730, filed Dec. 21, 2010, which is expressly incorporated herein by reference.

THE FIELD OF THE INVENTION

The present invention relates to devices and methods used to view an area when direct line-of-sight observation is not feasible. In some aspects, the invention relates to an optically guided medical tube and control unit assembly that may be used for prolonged and/or repeated viewing of an area that would otherwise be difficult or impossible to view with the naked eye, such as the interior anatomy of a human or animal. In other aspects, the invention relates to methods of using an optically guided medical tube and control unit assembly.

BACKGROUND

Medical tubes are used in a variety of medical procedures that require one end of the tube to be located inside the body while the other end remains outside the body. Such tubes can be useful in treating a patient over an extended period of time by, for example, repeated administration of medication, delivery of nutrients or oxygen, or removal of fluids. Proper placement and positioning of medical tubes is often critical to their effective use. For example, it is typically desirable to administer medication or deliver nutrients to a specific location in the body to maximize the efficacy of the medication or the benefits of the tube. However, placement of most medical tubes is often performed without immediate visual confirmation that the tube has been located at the proper location.

For example, medical tubes are often used to treat a patient if the patient has a compromised ability to obtain proper nutrition through oral intake. The medical tubes used for this treatment are more commonly referred to as nasogastric or nasoenteric feeding tubes. Placement of these feeding tubes is routinely performed in a number of clinical settings including emergency rooms, hospital wards and intensive care units totaling greater than 1.2 million tubes annually. Feeding tube placement, like placement of most other medical tubes, is commonly done without a visual aid to help medical personnel navigate the tube down the nose, through the esophagus and into the stomach or small intestine and confirm that the distal end of the tube is placed in its proper end location. Medical personnel advance the tubes through the patient's body blindly. Because the medical personnel cannot see the distal end of the feeding tube during advancement, the feeding tube can be incorrectly positioned during the process. In extreme cases, the distal end of the feeding tube may pass into the cranium and into the patient's brain, while the nurse or other practitioner continues advancing the feeding tube believing that it is properly entering the gastrointestinal tract.

More commonly, misplacement of the feeding tube results in other serious complications including lung placement or puncture or esophageal puncture. It is estimated that 3.2 percent of all blind nasoenteric feeding tube placements result in the feeding tube being disposed in the lung. In approximately 1.2 percent of placements, the patient will suffer a punctured lung. In approximately 0.5 percent of cases, the patient will die as a result of the procedure. It is estimated that in intensive care units alone, up to six thousand patients die each year from improperly placed feeding tubes.

Additionally, providing any feeding solution through the feeding tube into the lungs likely results in pneumonia with increased morbidity and mortality. Thus, it is critical to ensure verify that there has been proper placement of the feeding tube. Unfortunately, many common methods for doing so leave patients at substantial risk.

Proper placement of the tube is verified using a variety of tests, including chest x-ray, pH tests, auscultation, or fluoroscopy. However, these tests only attempt to confirm position after placement when complications may have already occurred. For example, if fluoroscopy or X-ray confirms that the feeding tube is actually disposed in the lung, it does so only after the possibility of lung puncture or other damage to the lung tissue. Additionally, while X-ray imaging and fluoroscopy are often used, both only provide a two dimensional indication of location, i.e. placement below the diaphragm. In multiple instances, confirmation of placement has been given when the feeding tube had actually passed through the lung and along the diaphragm, rather than being disposed in the gastrointestinal tract. Moreover, X-ray or fluoroscopic confirmation does not clearly confirm placement in the small bowel rather than the stomach. Small bowel placement is generally preferred to prevent the risk of aspirating feeding solution.

Additionally, some of these techniques have additional limitations and drawbacks. For example, fluoroscopic exams and X-Ray verification can cost $400 or more and can expose the patient and the practitioner to harmful radiation. If a patient is pregnant, a child or in poor health, exposure to such radiation may be highly undesirable. Additionally, the use of such verification procedures significantly prolongs the period of time that a patient must wait after a feeding tube is placed before feeding can begin. Because of this, the average time from ordering feeding tube placement to confirmation of placement and beginning of feeding is 22-26 hours. If the tube is placed improperly, the wait to begin feeding can take even longer as the process must be repeated. During this time, the patient is unable to obtain nourishment and any medications which may be delivered via a feeding tube.

Another complication which is common with patients receiving a feeding tube is that the patients are often not coherent. The patient may be partially sedated or may be delirious. Thus, it is not uncommon for a patient to pull out a feeding tube which has previously been placed. This requires repetition of the procedure, again subjecting the patients to the risks set forth above. Thus, a simpler, safer method for placing feeding tubes would be highly desirable.

An alternate method for placement and verification of feeding tubes is by use of an endoscope. Typically an endoscope is inserted into the mouth of the patient and advanced down until the endoscope has passed through the esophagus and at least into the stomach, and preferably through the pyloric sphincter and into the duodenum. In some applications, a guidewire is advanced to the proper location and the endoscope is removed. The guidewire is then manipulated to move it from the oral placement to a nasal placement, and a feeding tube is advanced along the guidewire into the desired location.

In other applications, the feeding tube is carried in a working channel (or along the side) of the endoscope. The feeding tube is sufficiently long that once the feeding tube has been placed, the endoscope can be removed over the feeding tube. The feeding tube is then cut and an appropriate adaptor attached for feeding.

While placement and verification using an endoscope is advantageous, it also has several drawbacks. One drawback is that using an endoscope usually takes considerable skill to steer the tip of the endoscope through complex and tortuous paths in the body, which can be made more difficult if the tip cannot be steered in multiple directions. Furthermore, endoscopy procedures are typically performed by physicians, often requiring a longer wait time before a properly trained physician is available to place the feeding tube, as opposed to the wait time if medical personnel other than a physician could place the tube.

Another drawback of using an endoscope to place a feeding tube is that, because the endoscope is typically placed through the mouth, an additional procedure must be used if the feeding tube is to be used nasoenterically. This involves advancing a structure through the nose and out the mouth, securing the end of the feeding tube (or a guidewire) to the structure, and then pulling the structure and the end of the feeding tube through the nose. Also, the procedure usually requires conscious sedation which increases the risk and cost of the procedure.

Additionally, an endoscope is a complex, expensive medical device. One significant cost associated with the manufacture of an endoscope can be the optical fibers used to transmit light and images. Devices that are designed to inspect the inside of the body of a human or animal are typically designed to allow medical personnel to perform additional functions inside the patient, other than just viewing the internal anatomy. Additionally, these devices must be able to navigate through narrow passageways in the body. Thus an optical fiber that is appropriate for use in such devices must be sufficiently narrow so that the device and any additional lumen for passing instruments, wires, etc., can comfortably traverse through narrow passageways in the body. Optical fiber with a small enough diameter, however, is typically more expensive. For example, the cost of an optical fiber made essentially of glass (1.0 OD) can be more than four times greater than the cost of an optical fiber made of plastic (1.8-2.0 OD) which performs similarly as the smaller, glass optical fiber. The larger optical diameter of the cheaper, plastic optical fiber, however, may limit the amount of space for additional lumens that may be used to perform additional functions.

Furthermore, because an endoscope is a complex and expensive medical device it is generally not discarded after use in one patient, but rather it is reused in subsequent patients. Prior to reuse of the endoscope, however, it must be properly prepared and sterilized to reduce the risk that an infection could be transmitted from one patient to another. The procedure of cleaning and disinfecting an endoscope is both time consuming and expensive and may involve mechanical cleaning, leakage testing, disinfecting the endoscope chemically for an appropriate amount of time, and then rinsing and drying the endoscope. Often this process must be accomplished by an individual properly qualified to perform the procedure.

Each of the above-referenced methods for placing a feeding tube also has problems with subsequently confirming that the feeding tube remains properly placed. As a patient moves, the distal end of the feeding tube can work its way out of the intestine and coil in the stomach. Depending on the particular concerns regarding the patient, it may be necessary to periodically confirm that the feeding tube is placed properly. This can require additional x-ray, pH tests, auscultation, or fluoroscopy, or the use of another endoscope to ensure that the feeding tube is properly placed. Each of these methods for confirming placement has the drawbacks mentioned above.

Although the current discussion has been directed at the disadvantages of current methods for placing a feeding tube, similar disadvantages exist with current procedures for placing other medical tubes. Such other procedures include placement of a jejunal extension tube in percutaneous gastrojejunal feeding tubes (PEGJ). Presently, for PEGJ tubes, the jejunal extension tube must be threaded through the existing gastrostomy tube or stoma into the small bowel. This is done using fluoroscopy or endoscopy to advance a wire into the small intestine and then a jejunal feeding tube is passed over the wire into the small intestine (jejunum). A jejunal extension tube with direct visualization and/or steering mechanism could perform the same task without the drawbacks of using endoscopy or fluoroscopy as noted previously.

Other situations include those in which prolonged visualization and access for irrigation/infusion and drainage would be beneficial. For example, in pancreatobiliary infections, it is not uncommon for the common bile duct (or associated duct) to become blocked and restrict fluid flow into the duodenum. An endoscope or other catheter based method is typically used to place a shunt or stent in the pancreatic duct or the common bile duct to allow proper drainage of pus from the pancreatobiliary ducts through the common bile duct into the duodenum. Once the situation has been alleviated, an endoscope or other device may be advanced back into the duodenum to remove the shunt or stent. Of course, it is often difficult to tell if the situation has been fully alleviated, if the device has become misplaced, or if the symptoms have simply been reduced.

In these procedures, as well as others in the body, it may be advantageous to provide continued viewing capacity both to ensure proper placement of the structure used for drainage, and to allow medical personnel to get a view of the affected area to determine whether and how quickly healing and/or drainage is taking place. In these clinical situations such a device can replace or assist fluoroscopy and/or endoscopy for guidance, placement, confirmation and reconfirmation. In addition, such an indwelling device can be used to drain pus or other bodily fluids from body cavities as well as provide a conduit for irrigation and infusion of medications including antibiotics.

Accordingly, it would be desirable to provide a medical tube which can be placed more conveniently and which can be used to confirm placement without the need for radiation or other traditional confirmation methods. Additionally, it would be advantageous if such medical tubes could be used, and methods for placing such medical tubes could be performed, by medical personnel other than physicians.

Thus, there is a need for an improved optically guided medical tube and control unit assembly and methods of using the same that reduces risks associated with the placement of medical tubes inside the body of a patient. The improved optically guided medical tube and control unit assembly should be readily reusable to confirm that the distal end of a medical tube has not been displaced after the medical tube has been associated with a patient over an extended period of time, for example about 30 minutes or more. It is desirable that the optically guided medical tube and control unit assembly is relatively easy to use and that it is relatively inexpensive to manufacture.

SUMMARY OF THE INVENTION

It is an object of the present invention to provide an optically guided medical tube and control unit assembly and methods of using the same.

According to one aspect of the present invention, an optically guided medical tube and control unit assembly may include tubing having an optical fiber extending therethrough coupled to or coupleable with a control unit having an image capturing device and a light source associated therewith. When the tubing is coupled to the control unit, the optical fiber from the tubing and the control unit may be aligned to allow light from the light source to be directed through the optical fiber to a distal end of the tubing so that images may be collected with the image capturing device.

According to another aspect of the present invention, an optically guided medical tube and control unit assembly may include a steering mechanism. The steering mechanism may comprise tubing having a wire coupled to or coupleable to the control unit. The wire may provide for motion control of the tubing, allowing a user of the assembly to guide or steer the tubing through turns in anatomical or other structures.

According to still another aspect of the present invention, the steering mechanism may comprise tubing having a plurality of wires coupled to the control unit to provide multidirectional movement of the tubing.

According to yet another aspect of the present invention, the steering mechanism may comprise a wheel configured to receive one or more wires associated with the tubing. For example, the wheel may receive one wire or wire segment which wraps around the tubing in a clockwise direction and a second wire or wire segment which wraps around the tubing in a counterclockwise direction. Structures in or on the wheel may operatively engage structures on the control unit, such as gears, to thereby couple the wheel to the control unit and enable control of the wheel via the control unit. Actuation of the gears may be accomplished using a device on the control unit, such as a thumbwheel, slide or other movable control structure, to control movement of the wires, and thus the tubing.

In another aspect of the invention, the optical fibers and wire of the tubing may be coupled to the control unit via a coupling adaptor. The coupling adaptor may also comprise a wheel for receiving the wires of the tubing. The coupling adaptor may be configured to be removably connected to the control unit so as to allow quick and simple engagement of the steering mechanism with the control unit and alignment of the optical fibers with the image capturing device and light source. Alignment of the optical fibers with the image capturing device and light source may be facilitated by including chamfered openings on the control unit at locations where the optical fibers couple to the control unit. Additionally, it may be desirable to construct the coupling adaptor to be lightweight and small enough to go substantially unnoticed when it is intended that a medical tube will be associated with a patient for a prolonged period of time. Thus, for example, the coupling adaptor may remain attached to the medical tube when detached from the control unit.

In accordance with another aspect of the present invention, the tubing of the optically guided medical tube and control unit assembly may be comprised of a plurality of sections operatively connected. The sections of tubing may comprise a first tubing section having a distal end configured for placement inside a patient's body and a proximal end configured for removably connecting to the control unit, and a second tubing section configured to engage the tube mounting unit. The first tubing section and the second tubing section may be operably connected to each other via a tubing connector.

According to another aspect of the present invention, the second tubing section may be disposed of after tube placement to thereby substantially eliminate the disadvantages associated with processing of an endoscope in between uses on different patients.

In accordance with another aspect of the invention, the first tubing section and the second tubing section may be operatively connected via a tube adaptor. The tube adaptor may also be used after the medical tube has been placed in a patient to connect to devices configured to deliver nutrients or medications, and/or to connect to devices designed for flushing or insufflation. An optical medical tube may include multiple tube adaptors that may be removably connected to a coupling adaptor which couples the optical medical tube to the control unit. The tube adaptors may be removably connected to a coupling adaptor so as to enable easy coupling of the optical medical tube to the control unit during placement of the tube in a patient and coupling of the optical medical tube to devices configured for administering nutrients or medicines and/or devices configured for flushing, aspiration, and insufflation.

According to another aspect of the present invention, the control unit may include a tube mounting unit comprising a plurality of retention locations for engaging tubing. The plurality of locations on the tube mounting unit where tubing is engaged may include a channel for holding a tubing segment, a retention member for selectively holding the tubing segment in the channel and an occlusion member adjacent said channel for selectively occluding flow through the tubing segment held in the channel. Additionally, the control unit may include an actuation mechanism which is operatively connected with the retention member and/or the occlusion member and configured to move the occlusion member between a plurality of positions. Thus, for example, the tube mounting unit can accommodate and control the flow through disposable tubing sets while providing for reuse of the control unit without the significant cleaning process required of endoscopes.

According to one aspect of the present invention, tubing may be coupled to the control unit via the tube mounting unit and actuation mechanism by applying a force to the actuation mechanism at a first end which may move the occlusion member into a load position to thereby allow tubing to be placed in the channel. Once a tubing segment is placed into the channel, the retention member may be moved to a closed position by releasing the actuation mechanism to secure the tubing segment in the channel.

In accordance with another aspect of the present invention, the occlusion member can be moved selectively between an open position wherein the occlusion member does not occlude flow through the tubing segment and a closed position wherein the occlusion member may substantially occlude fluids from passing through the tubing. The occlusion member may be moved between the closed position to various open positions by applying force to a second end of the actuation mechanism. When in open positions, the occlusion member may substantially prevent the tubing from exiting the channel of the tube adaptor unit while allowing a desired volume of fluid to pass through the tubing.

According to still another aspect of the present invention, the actuation mechanism of the control unit may comprise a cable and lever actuation system. The cable and lever actuation system may interact with the actuation mechanism to control flow through a plurality of tubing segments when the tubing segments are mounted on the control unit.

One aspect of the present invention may include an optical medical tube comprising an optical fiber releasably connected thereto. For example, the optical fiber may comprise a release, such as a push clip release, that enables the optical fiber to be releasably connected to a coupling adaptor coupled to the optical medical tube. Thus, the optical fiber may be reusable with more than one medical tube.

According to another aspect of the present invention an optical medical tube may include a stylet having a generally X-shaped cross-section. The generally X-shaped cross-section of the stylet may include a central lumen 1265 which allows an optical fiber having a larger outer diameter (e.g. between about 1.8 mm and 2.0 mm) to be used with the optical medical tube while maintaining sufficient space to administer medications and/or nutrients over a prolonged period of time, and/or perform flushing, aspiration or insufflation procedures. The X-shaped shaped stylet may also have a cutaway section adjacent the tip which aids steering of the optical medical tube during placement.

According to another aspect of the present invention, the optical medical tube may include a tube tip which may provide alignment of imaging. The tip may be connected to the tube so that there is a standoff or gap between the tip and the stylet so as to also facilitate flow of nutrients and medication from a fluid pathway defined by a groove in the stylet and the inner wall of the medical tubing. The gap may also facilitate flushing, aspiration, and/or insufflation by ensuring that sufficient space exists between the tube tip and one or more lumens in the stylet.

These and other aspects of the present invention are realized in an optically guided medical tube and control unit assembly and methods of using the same as shown and described in the following figures and related description. It will be appreciated that not all aspects of the system or method need be present in any particular embodiment and that embodiments may include a variety of different aspects of the present invention while not including other aspects of the invention as disclosed herein. Thus, various aspects of the system and method set forth are independently claimed in the appended claims, which define the invention or inventions contained herein.

BRIEF DESCRIPTION OF THE DRAWINGS

Various embodiments of the present invention are shown and described in reference to the numbered drawings wherein:

FIG. 4 shows an exploded, perspective view of an optically guided feeding tube system including a feeding tube and a control unit formed in accordance with another aspect of the present invention, while

Figure 1A:
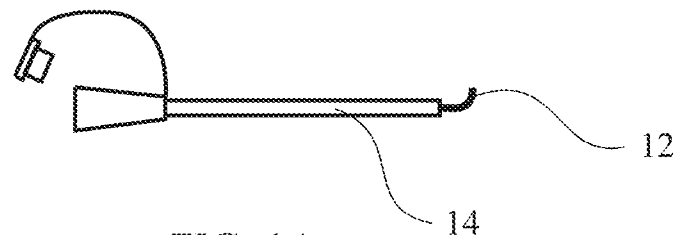
FIGS. 1A through 1C illustrate various components of devices used for placing feeding tubes in accordance with the prior art, including a feeding tube having a guide wire (FIG. 1A), an intubation tube with a guidewire (FIG. 1B) and a close-up of a curved end of a guidewire (FIG. 1C)

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Thus, it may be considered that any aspect shown in one drawing could be used in connection with structures shown in another drawing. Similarly, every embodiment need not accomplish all advantages of the present invention.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts and by the terms set forth in the claims. It should also be understood that terminology employed herein is used for the purpose of describing particular aspects of the invention only and is not intended to limit the invention to the aspects or embodiments shown.

It must be noted that, as used in this specification and the appended claims, the singular forms "a," "an," and "the" may include plural referents unless the context clearly dictates otherwise. Thus, for example, reference to "an optical fiber" may include one or more of such optical fibers, and reference to "the lens" may include reference to one or more of such lenses.

As used herein, "subject" or "patient" refers to a mammal that may benefit from the devices and methods of the present invention. Examples of subjects include humans, and may also include other animals such as horses, pigs, cattle, dogs, cats, rabbits, and other land and aquatic mammals.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The Invention

An integrated feeding tube device is provided that can safely and effectively place and verify placement of the feeding tube in the gastrointestinal tract of the patient. The device may include a feeding tube operable to deliver a nutritional and/or medicinal substance to the gastrointestinal tract, a steering system used to help guide the feeding tube to the desired location in the gastrointestinal tract, and an optical system including structures to provide light into the gastrointestinal tract, and an optical system having image transmitting device such as flexible optical fibers and a lens or a camera for transmitting images of the gastrointestinal tract. Components of the system, namely the optical system and the steering system, may be all integrated into the feeding tube so as to enable directed placement of the feeding tube, confirmation of placement of the feeding tube and to enable repositioning of the distal end of the tube if necessary.

Feeding tubes as described herein can be any type of feeding tubes known, including, without limitation, nasogastric and nasoenteric tubes and percutaneous gastrostomy, percutaneous gastrojejunostomy and percutaneous jejunal feeding tubes. Such tubes can be made of any material known in the feeding tube industry. Generally any flexible plastic or polymeric material can be used. The feeding tube is generally hollow and capable of delivering nutritional, medicinal, or other oral agents to a subject. The diameter of the feeding tube can vary depending on the intended use, e.g. the characteristics of the subject or the duration of feeding tube use. For example, a tube intended for use with infants and small children will typically have a smaller diameter and delivery capacity than those intended for use with adults. Feeding tubes are well known in the art, and any such tube or tube configuration would be considered to be within the present scope.

The optical system of the integrated feeding tube device can include one or more light carrying members, which may include fiber optic fibers or other light conveying structures and optical transmission mechanisms such as optical fibers attached to one or more lenses or a miniature camera. Collectively, the components of the optical system function to deliver light to the distal end of the device, to provide the ability to visually observe an area around the distal end of the feeding tube during placement within the subject. This visual observation can aid a practitioner during placement of the device and in verifying proper placement of the device within the gastrointestinal tract. The resolution of images or video produced by the optical system can be of any level, provided sufficient resolution is obtained for a practitioner to be able to quickly and accurately identify the type of tissue, body lumen or cavity seen through the optical system. For example, it is desirable that a practitioner be able to quickly distinguish between the trachea and the esophagus, and most critically that the practitioner can ensure that the tissue being seen is not the bronchi or lung tissue.

While endoscopes usually provide high resolution because they are often used for closely examining tissue for diagnosis or carrying out procedures, it is not necessary for the feeding tube to provide high resolution. Although high resolution can be used, lower resolution images can be sufficient to verify proper placement of the integrated feeding tube device in the gastrointestinal tract and ensure that the feeding tube is not in the lungs.

The optical system can have depth of field range of from about 2 mm to about 100 mm, and can have a field of view of from about 30° to about 140°. In one embodiment, the optical system can have a field of view of from about 60° to about 125°.

When used, the optical fibers used in the optical system can be made of any material known in the art including, but not limited to silica, fluorozirconate, fluoroaluminate, chalcogenide, and plastic optical fibers such as polymethylmethacrylate, and the like. In one embodiment, the optical fibers can be made from polymethylmethacrylate. Additionally, the lenses of the optical system can be made from any material known in the lens art including, but not limited to silica and polymers such as polymethylmethacrylate. In one embodiment, the lenses can be made from gradient index polymethylmethacrylate. In the event a camera is used, a camera such as a cmos camera works well because the can be acquired in a diameter of about 1 mm and are not overly expensive. However, it will be appreciated that other cameras may be used.

One or more of the optical fibers (or some other structure) can transmit light for illuminating an area at the end of the integrated tube device, and one or more other optical fibers can carry the visual images from the end of the device to a viewing component which, as discussed below, may be formed as part of a control unit. In the alternative, a cable or wire could carry images from a camera. It will be appreciated that the present invention includes numerous different aspects which may stand alone or which may be used in combination. Thus, the presence of a feature in one of the figures is for illustration purposes and it will be appreciated that any of the devices shown in the drawings could include features shown in other drawings, but which have been omitted to keep the drawings readily understandable.

In one embodiment, at least one optical fiber(s) provides illumination at the distal end of the integrated feeding tube device of at least 800 Candelas. In another embodiment, at least one optical fiber(s) provides illumination at the distal end of the integrated feeding tube device of at least 1000 Candelas. In the alternative, or in conjunction, Infrared light may be used as cameras can be used to pick up multiple wavelengths of light, or a camera which provides images based solely on Infrared light may be used.

Figure 1B:
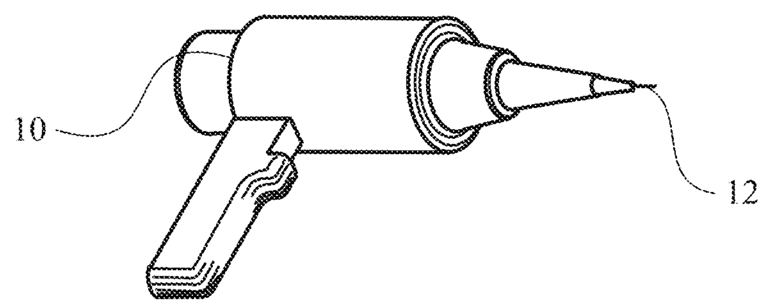
Figure 1C:
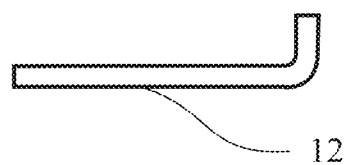

Turning momentarily to FIGS. 1A through 1C, there are shown prior art mechanisms for placing a feeding tube. One is an intubation device 10 (FIG. 1B) with a guidewire 12 extending therefrom which may be inserted into the mouth of a patient. The other is a nasoenteric feeding tube 14 (FIG. 1A) with a guidewire 12. FIG. 1C is a close-up of the curved end of a guidewire which can facilitated steering or placement. Such devices can be used for blind placement or with an endoscope. However, as will be explained below, the present invention has several marked advantages over blind and endoscopic placement of feeding tubes.

Figure 2A:
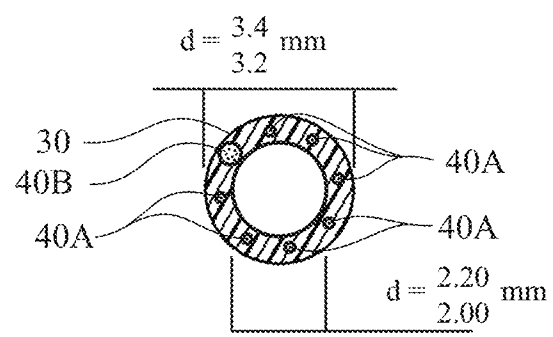
FIG. 2A is a cross-sectional view of a nasoenteric feeding tube formed in accordance with the principles of the present invention.

Turning now to FIG. 2A, there is shown a cross-sectional view of a feeding tube 30 having an optical system integrated into a wall of the feeding tube. In such an embodiment, optical fibers can be incorporated directly into the feeding tube 30 during manufacturing of the tube. Thus, optical fibers 40A and 40B are directly incorporated into the feeding tube wall. Fibers 40A (which may be for example 30 μm fibers or other sized fibers) are used for conveying light to the distal end of the feeding tube 30, while fibers 40B (which may be for example 0.5 mm fibers or other sized fibers) typically terminate in a lens and convey an image of the tissues adjacent the distal end of the feeding tube 30 to a viewing mechanism, such as an eyepiece or a monitor (not shown in FIG. 2A). It should be noted that the dimensions shown in FIG. 2A are merely exemplary, and are not to be seen as limiting the scope of the present invention.

While the feeding tube 30 may be used with an intubation device 10 and/or with a guide wire as shown in FIGS. 1A and 1B, in a presently preferred embodiment neither the intubation device 10 nor a feeding tube having a guidewire is needed.

The lens and fibers 40*a*, 40B form an integrated optical system in the feeding tube 30. Images provided by the optical system can be viewed using an image viewing component (not shown in FIG. 1). The image viewing component can be any viewing device known in the art. In one embodiment, the image viewing component may include an eyepiece that is operably connected to the proximal end of the optical system 40*b*. By looking through the eyepiece a practitioner can view the image of tissue at the distal end 30A of the feeding tube 30. The practitioner can use the image to guide the feeding tube 30 to its desired location and/or verify the proper placement of the device based on the tissues observed.

The eyepiece can optionally include a lens that enhances or enlarges the image. While FIG. 1B shows an intubation device, one advantage of the present invention is that intubation is generally not necessary to properly place the feeding tube 30. Rather, a feeding tube 30 (or 130 as set forth below) may be placed more quickly and with less discomfort by advancing the feeding tube through the nasal canal and into the gastrointestinal tract without the need for radiological confirmation prior to feeding.

Figure 2B:
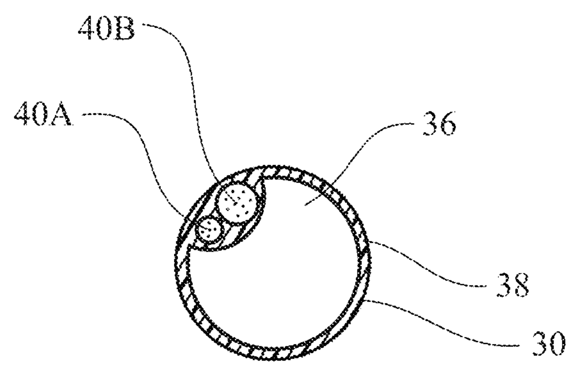
FIG. 2B is a cross-sectional view of an alternate configuration of a feeding tube formed in accordance with the present invention.

Another example of an embodiment of the optical fibers being incorporated directly into the feeding tube wall (or in a lumen formed in the wall) is shown in FIG. 2B. The feeding tube 30 includes three lumens (or channels within the outside wall). A first large lumen 36 is configured for delivery of feeding solution. Those familiar with enteral feeding solutions will appreciate that they can be somewhat viscous. Thus, it is desirable to have a lumen 36 which will facilitate the passage of the solution without making the feeding tube 30 uncomfortably large to pass through the patient's nasal canal. The other two lumens or formation in the exterior wall 38 are the light source 40A and the lens and optical fibers 40B which carry an image to the image viewing system discussed above. In the alternative, the optical fibers for lighting and viewing may be disposed in a common bundle (typically coaxially with optical viewing fibers surrounded by lighting fibers), or a lighting mechanism and camera could be used. The other lumen can then be used for steering in a manner discussed below.

Figure 3:
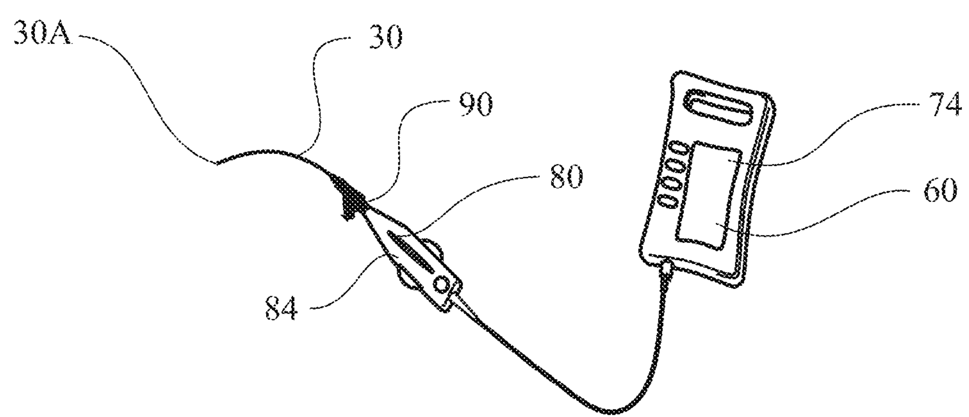
FIG. 3 is a perspective view of an optically guided feeding tube system in accordance with one aspect of the invention.

As shown in FIG. 3, the optical system 40 can be attached to a display, such as an electronic screen 74 that receives and displays the image from the optical fibers. The electronic screen 74 can be of any type or variety known in the art including, but not limited to small hand-held screens, computer monitors, televisions, etc. Also shown in FIG. 3 is a steering system 80 of the integrated feeding tube 30. By providing one or more wires in the feeding tube 30, a control unit 84 can be connected to the wire(s) which is capable of guiding the distal end of the integrated feeding tube device, thereby facilitating the placement of the device in the gastrointestinal tract. A variety of steering mechanisms are contemplated, all of which are intended to be within the present scope. In one embodiment, the steering system can include a wire that is capable of causing the distal end 30A of the integrated feeding tube 30 to bend when moved in one direction (typically longitudinally) and to straighten the feeding tube when moved in the opposite direction. In another embodiment, the steering system 80 can include a polymeric composition that can be manipulated to cause the distal end of the integrated feeding tube device to bend. The amount or degree of bend in the end of the integrated feeding tube device can be varied depending on the type of the steering system and the intended population for the device. In one embodiment, the steering system can provide a turning radius of about 2 cm to about 3 cm. Steering systems, such as those described above, can be operated by steering controls that are located at or near the proximal end of the integrated feeding tube device.

In another embodiment, the integrated feeding tube device can include a release coupling 90 to allow one or both of the image viewing component 60 and/or the steering control 80 to be disconnected from the feeding tube 30. Such a release coupling can be located on the feeding tube 30 such that the coupling remains external to the subject during placement of the tube. Releasing and removing the steering controls 80 and the image viewing components 60 allows the integrated tube to be less bulky, thus decreasing discomfort experienced by the subject while the tube is in position. Additionally, releasing and removing these systems allows the image viewing component 60 and steering control 80 to be reused. The ability to reuse these components of either with other feeding tubes, or with the same feeding tube 30 at a later time can substantially reduce the costs associated with the device and its use as compared to endoscopes and other means of confirming the placement of the feeding tube 30.

In some embodiments it may also be important that the feeding tubes of the present invention have couplings that properly articulate with standard feeding tube adapters. These standard adapters are used to couple the feeding tubes to feeding sets that are used to feed subjects or to deliver medicaments to subjects. In such a case, a feeding tube of the present invention can be placed in the subject, the steering and image viewing systems 80 and 60, respectively, can be decoupled, and feeding tube 30 can be coupled to a feeding set using a standard adapter.

In another embodiment of the invention, a method of placing a feeding tube inside a gastrointestinal tract of a subject is provided. The method includes providing an integrated feeding tube 30, such as described above, and inserting a distal end of an integrated feeding tube device into the nasal passage of a subject. The integrated feeding tube 30 is then positioned inside the gastrointestinal tract of the subject, such as by using the steering system 80 of the integrated feeding tube. After positioning of the integrated feeding tube 30, proper placement in the gastrointestinal tract of the subject can be visually verified by using the optical system 40B and the visualization component 60. It should be noted that the steering and optical system located within the feeding tube can increase the stiffness of the tube, thus facilitating tube placement in the subject.

Once placed, the feeding tubes 30 of the present invention can be typically maintained in the gastrointestinal tract for a period of up to 30 days. In some cases, the feeding tubes can be maintained for even longer periods of times. Removal of the integrated feeding tubes 30 of the present invention can be accomplished through the known methods in the art.

As with all feeding tubes, the integrated feeding tube devices of the present invention can be subject to frictional resistance during placement. In order to reduce frictional forces on the device, it can be desirable to lubricate the device prior to its placement in the subject. Biocompatible lubricants that can be used are well known in the art and include those that are currently used in feeding tube placement and endoscopy.

One distinct advantage of feeding tubes 30 of the present invention is that the optical system 40B can be used throughout the life of the feeding tube. At any time a practitioner wishes to confirm placement of the distal end 30A of the feeding tube 30 or wishes to view tissue in the gastrointestinal tract adjacent the distal end of the feeding tube, he or she need only reattach the image viewing system 60 and observe. With prior art feeding tubes, x-ray, fluoroscopy or other viewing methods that are both expensive and time consuming must be used. Additionally, the patient is exposed to additional radiation.

Figure 4:
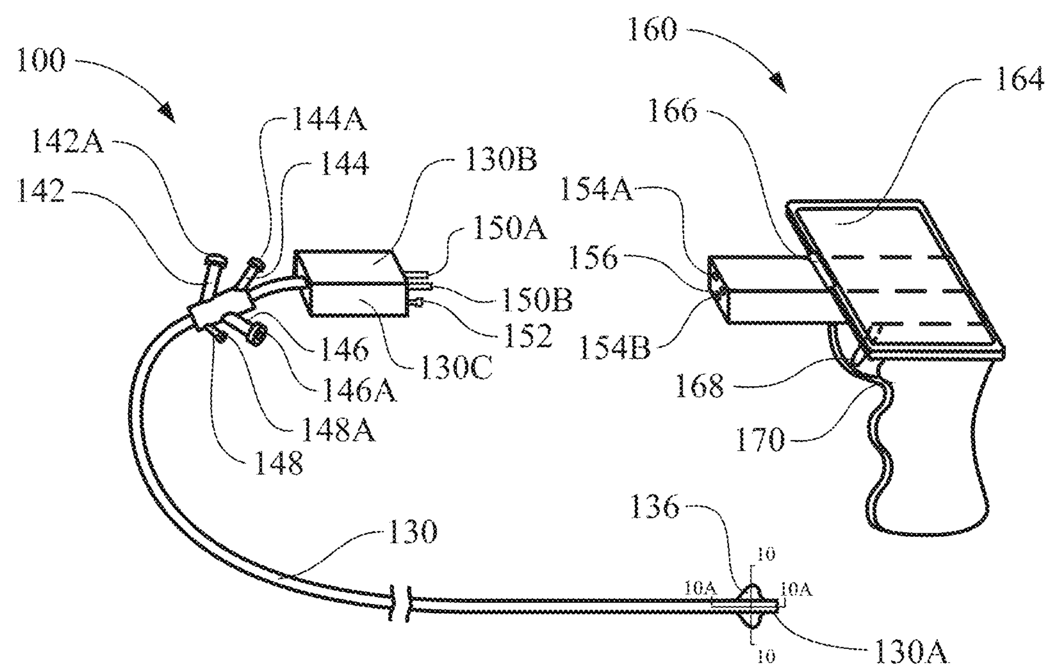

Turning now to FIG. 4, there is shown a perspective view of an optically guided feeding tube system, generally indicated at 100 formed in accordance with another aspect of the present invention. The feeding tube system 100 includes a feeding tube 130. At a distal end 130A the feeding tube 130 includes a port through which feeding solution, medication, or the like can be delivered to the gastrointestinal tract, and one or more openings through which light can be directed against tissue in the gastrointestinal tract and images thereof communicated to a proximal end 130B of the feeding tube 130.

Disposed adjacent the distal end 130B of the feeding tube 130 is an anchoring device 136. The anchoring device 136 can be a balloon, a coil, a stent or other structure which helps to hold the distal end 130A of the feeding tube 130 in the desired location in the gastrointestinal tract.

Disposed adjacent the proximal end 130B are a plurality of ports 142, 144, 146 and 148. Port 142 has a coupling or adapter 142A for attachment to an enteral feeding solution line and communicates with the feeding lumen in the feeding tube. Port 144 is disposed adjacent thereto and may include a coupling or adapter 144A configured to receive a syringe or other fluid source which is used to periodically flush the feeding lumen. Port 146 is provided to flush another lumen of the feeding tube 130 so as to clean the optical system as will be explained in additional detail below and may include a coupling or adapter 146A configured for receiving a syringe, etc. Port 148 may be provided to inflate the anchoring device 136 when such is a balloon, and may also have a coupling or adapter 148A configured to receive a syringe, etc.

As shown in FIG. 4, a feeding tube adapter 130*c* is disposed at the proximal end 130B of the feeding tube 130. The adapter 130*c* may have a plurality of projections which are used to operate the visualization and steering capabilities of the feeding tube 130. Projection 150A comprises a portion of the optical system (typically fiber optic fibers) which transmit light through the distal end 130*b*. To effectuate the transmission of light, the fiber optic fibers 150A (or other transmission medium) engage an opening 154A in a control unit, generally indicated at 160. Inside the control unit is a light source which is conveyed through the optical system to cast light on tissue in the gastrointestinal tract. The optical system may provide concentric orientation or parallel orientation between transmission of light and images whether by fibers or by a camera, etc.

The second projection 150B engages an opening 154B in the control unit 160 and are disposed in alignment with a camera or other source for converting images. It will be appreciated that in a presently preferred embodiment, the projection 150B may be fiber optic fibers, but other transmission mediums can be used, such as a cable attached a camera in the feeding tube. Image conveyed to the control unit 160 can be displayed on an image viewer, such as a video display screen 164. While nearly any viewable size may be used, a 2×3 inch (5×7.6 cm) video screen is presently preferred as it is large enough to clearly see the tissue at the distal end 130A of the feeding tube 130, but can be kept immediately adjacent the feeding tube and other controls to prevent the practitioner from having to look away from the feeding tube while it is being advanced. Additionally, the screen can be pivotably attached by an attachment member 166 to the control unit to enable it to be pivoted into a position most comfortable for the practitioner.

The adapter 130*c* may also include a cable 152 which projects outwardly therefrom. The cable 152 can nest in an opening 156 in the control unit 160. A steering mechanism, such as a trigger 168 may be moved backward or forward to advance the cable toward or away from the distal end 130A of the feeding tube 130. As will be explained below, this enables the bending or straightening of the distal end 130A of the feeding tube 130 and facilitates advancement of the feeding tube through the gastrointestinal tract.

The control unit 160 may also include a handle portion 170. The handle portion 170 gives the practitioner an ergonomic structure with which to push the feeding tube 130 forward. It also facilitates twisting the feeding tube 130 if necessary for proper advancement.

Figure 4A:
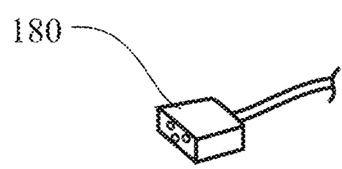
FIG. 4A shows an alternate adapter for a control unit.

While the control unit 160 is desirable for placement, if the patient has a condition that suggests frequent monitoring of the gastrointestinal tract, the control unit 160 could be removed and the adapter 130*c* coupled to an adapter 180 (FIG. 4A) for a video monitor for use on a long term basis by the practitioner or other medical personnel may be used.

Figure 5:
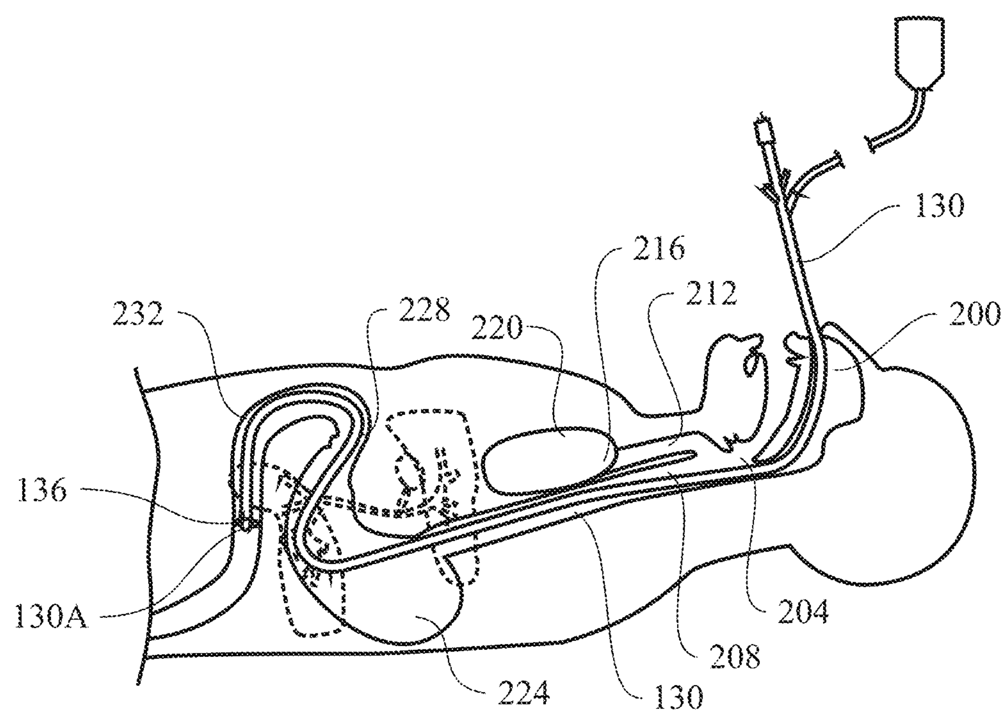
FIG. 5 shows a cross-sectional view of a patient being fed with a nasoenteric feeding tube placed in the person in accordance with principles of the present invention.

With reference to FIG. 5, there is shown a cross-sectional view of a patient (in this case a human although other animals including, but not limited to, horses, cows, pigs and other vertebrates, may be "patients" as well) being fed with a nasoenteric feeding tube placed in the patient in accordance with principles of the present invention. The distal end 130A of the feeding tube 130 is passed through the nasal canal 200 and past the pharynx 204. Care is taken that the distal end 130A advances down the esophagus 208 rather than into the trachea 212 and into the bronchi 216 and lungs 220. Advancing the feeding tube into the trachea, bronchi and lungs can result in numerous medical problems, including damage to the trachea and the bronchi and potentially a puncture of the lungs. Additionally, delivery of feeding solution in the lung can be catastrophic. Thus, the prior art has used a variety of expensive and time consuming procedures to ensure that the feeding tube is positioned properly.

Once placement in the esophagus is confirmed, the distal end 130A of the feeding tube 130 is advanced down into the stomach 224. In some situations, such placement may be acceptable. However to avoid reflux, aspiration and other concerns, it is usually preferred to pass the feeding tube through the pyloric sphincter 228 and into the duodenum 232. Once the distal end 130A is sufficiently into the intestines, the anchoring device 136, such as a balloon, coil or stent, may be deployed, to help hold the feeding tube 130 in place.

Not only is placement of the feeding tube 130 of the present invention safer than blind placement, it is anticipated that the procedure of placing the feeding tube 130 will, on average, take about one-fourth to one-third the amount of time as blind placement, as the practitioner does not have to move as slowly when he or she can verify the location of the distal end 130A of the feeding tube 130. This is in addition to the substantial saving in time by not requiring fluoroscopic, X-ray or other radiological confirmation of placement of the feeding tube. Thus, a patient may be able to begin receiving nutrition or medication within, for example, 20 minutes to half-an-hour instead of 24 hours. Additionally, the present procedure is better than use of an endoscope because the tube does not need to be advanced orally and then pulled back up through the nasal canal, saving both time and discomfort to the patient. Additionally, there is a substantial cost savings as there is no need to re-sterilize an endoscope.

Figure 6A:
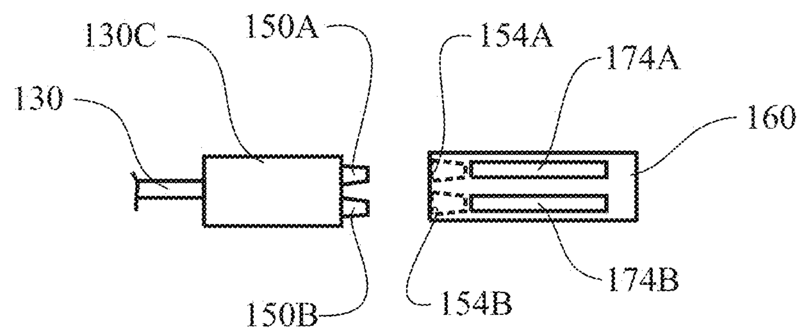
FIG. 6A shows a close-up view of a control unit adapter disposed at or adjacent the proximal end of the feeding tube.

FIG. 6A shows a close-up view of a control unit adapter 130*c* disposed at or adjacent the proximal end of the feeding tube. Each of the projections 150A and 150B are slightly tapered or conical and are designed to nest in tapered receptacles 154A and 154B reducing the potential for misalignment of the fiber faces. Receptacle 154A is disposed in alignment with a light source 174A and receptacle 154B is disposed in communication with a camera 174B or other image rendering device. In the event that the optical system in the feeding tube included a camera, receptacle 154B typically would be disposed in more direct communication with the display 164. The projection(s) can also be configured to provide for concentric orientation of the fibers.

Figure 6B:
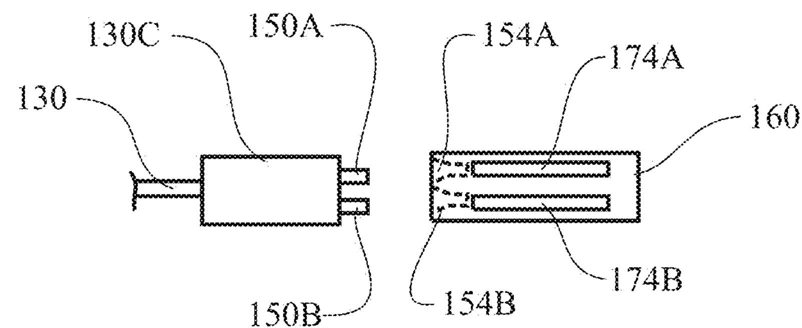
FIG. 6B shows a close-up view of an alternate configuration of a control unit adapter of the feeding tube.

FIG. 6B shows a close-up view of an alternate configuration of a control unit adapter 130*c* of the feeding tube 130. Rather than tapered projections, the projections 150A and 150B are generally cylindrical, but the receptacles 154A and 154B are tapered. It will be appreciated that numerous different configurations could be used. For example, the projections could also have a squared or rectangular cross-section.

Figure 6C:
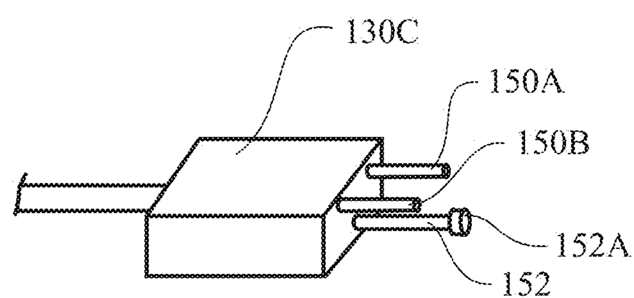
FIG. 6C shows a close-up perspective view of the control unit shown in FIG. 6B.

In FIGS. 6A and 6B, the cable 152 was omitted for clarity. If the feeding tube 130 includes a wire or cable for selectively straightening or curving the distal end of the feeding tube, the control unit 160 will preferably have a steering mechanism. FIG. 6C shows a close-up perspective view of the control unit adapter 130*c* including the distal end of the cable 152. As shown, the cable includes an engagement member 152A, which may be a ball, a ring, a knob or other mechanism wherein the control unit can engage and hold the wire so that the wire may be pulled away from or pushed toward the distal end of the feeding tube. As will be discussed below, the movement of the wire can bend a straight ended wire, or can straighten a distal end which is preformed with a curve. Such a structure can also be used to deploy a coil anchor as will be discussed below.

Figure 7:
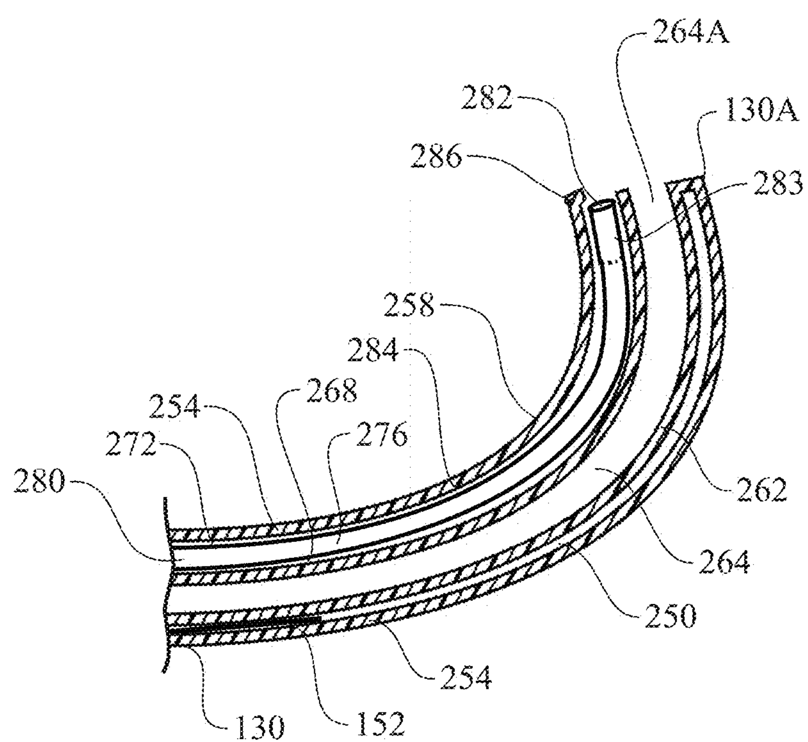
FIG. 7 shows a close-up cross-sectional view of the distal end of a feeding tube made in accordance with principles the present invention wherein the feeding tube can be steered during placement.

Turning now to FIG. 7, there is shown a close-up view of the distal end 130A of the feeding tube 130. The retaining device, such as a balloon, coil, stent, etc., is not shown for clarity, but may be included on such a device. However, the feeding tube may be used without any anchoring mechanism. The distal end 130A is pre-formed with a curvature. The curvature may have a radius of about 2 cm, or could have greater or lesser curvature depending on the desire of the practitioner.

The feeding tube 130 includes a lumen 250 which is typically disposed along the outer wall 254 of the feeding tube opposite the inner curvature 258. The distal end 152B of a cable or wire 152, which may have a resistance to bending which is stronger than the inherent formation of the distal end 130A of the feeding tube 130, is disposed in the lumen 250. As the wire 152 is advanced toward the distal end 130A of the feeding tube, the wire causes the distal end of the feeding tube to straighten. Thus, by advancing or withdrawing the wire 152, the practitioner can control the amount of curvature which is present at the distal end 130A of the feeding tube 130. In the embodiment shown in FIG. 4, this is done by moving the trigger 168. Pulling the trigger 168 will push the wire toward the distal end 130A of the feeding tube 130, straightening the feeding tube, while pushing the trigger 168 forward will withdraw most of the wire 152 and allow additional curvature in the distal end.

Also shown in FIG. 7 is an inner wall 262 which divides the lumen 250 carrying the steering wire 152 from a feeding lumen 264. Typically the feeding lumen 264 will be the largest lumen so as to accommodate the viscosity present in some feeding solutions. The feeding lumen 264 typically ends in an open port 264A at the distal end 130A of the feeding tube 130, while the steering lumen 250 typically will be closed at the distal end.

The feeding lumen 264 is bordered by another wall 268. Wall 268 and the outer wall 254 along the interior side form a third lumen 272 which, as explained below, includes an optical system 276. The optical system 276 may include a plurality of fiber optic fibers, generally shown as a single cable 280 and a lens 282. In the alternative a camera 283 may be disposed adjacent the end of distal end 130A and the cable 280 used to transmit pictures from the camera. While the optical system 276 could fill the entire third lumen 272, a void 284 may be left running along the third lumen which will allow fluid to flow in the lumen along side the optical system 276. (In multiple places in the figures, the optical system is shown with a lens 282 at the end of fiber optics and camera 283. It will be appreciated that these can be in the alternative or could be used in combination.)

The void 284 extending in the third lumen 272 along the optical system 276 allows, a cleaning fluid, such as saline solution or air, to be injected through the third lumen and help clean the lens 282. (If a camera 283 were used waterproofing material could be added if necessary). Directing the cleaning fluid may be done, for example, by a deflecting projection 286 disposed on the outside wall 254. As saline solution or other cleaning fluid is injected through the third lumen 272, the solution is deflected across the lens 282, to thereby clean the lens and provide better visibility. (The use of air can also be advantageous as injecting air inflates the gastrointestinal tract and can make visualization of tissue adjacent the feeding tube easier.)

Figure 8:
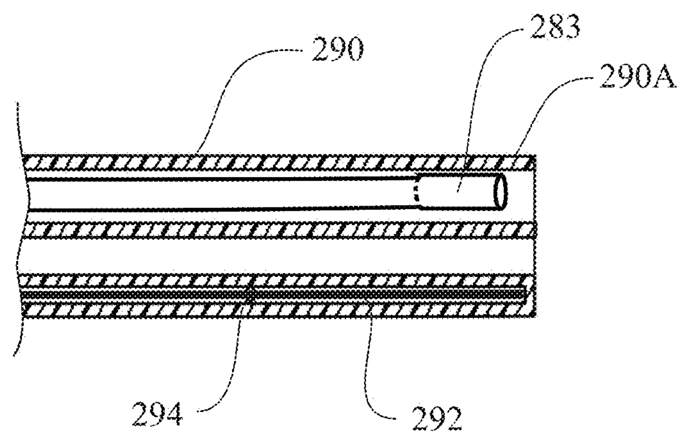
FIG. 8 shows a close-up cross-sectional view of the distal end of a feeding tube made in accordance with the present invention made in accordance with principles of the present invention.

Turning now to FIG. 8, there is shown a close-up, cross-sectional view of the distal end of a feeding tube made in accordance with the present invention made in accordance with principles of the present invention. Unlike feeding tube 130 shown in FIG. 9, the feeding tube 290 shown in FIG. 8 is generally straight. A wire 292 may be attached adjacent the distal end 290A of the catheter. The wire 292 is used to curve the distal end 290A of the feeding tube to assist in steering the feeding tube as it is advanced. This can be accomplished by the wire 292 passing through a neck 294 and is offset such that pulling the wire toward the proximal end of the feeding tube causes the end to defect.

In the alternative, the wire 292 could be formed from a memory shaped material such that the application of a current to the wire causes the distal end of the wire to deflect to thereby turn the distal end 290A of the feeding tube 290.

Figure 9:
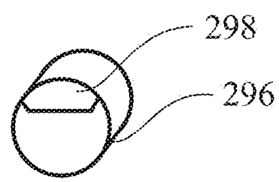
FIG. 9 shows a perspective view of an end cap configured for placement on the distal end of a catheter in order to control fluid flow for cleaning the distal end of the optical system.

Turning now to FIG. 9, there is shown a perspective view of an end cap 296 configured for placement on the distal end of a catheter in order to control fluid flow for cleaning the distal end of the optical system. The end cap 296 includes a deflector projection 298. As with the deflector projection 286 in FIG. 7, the deflector projection 298 is used to direct fluid flow so that when the end cap 286 is attached to the end of the feeding tube, the projection directs fluid flow to the lens on the optical system to thereby clean the optical system of feeding solution or other material.

Figure 10:
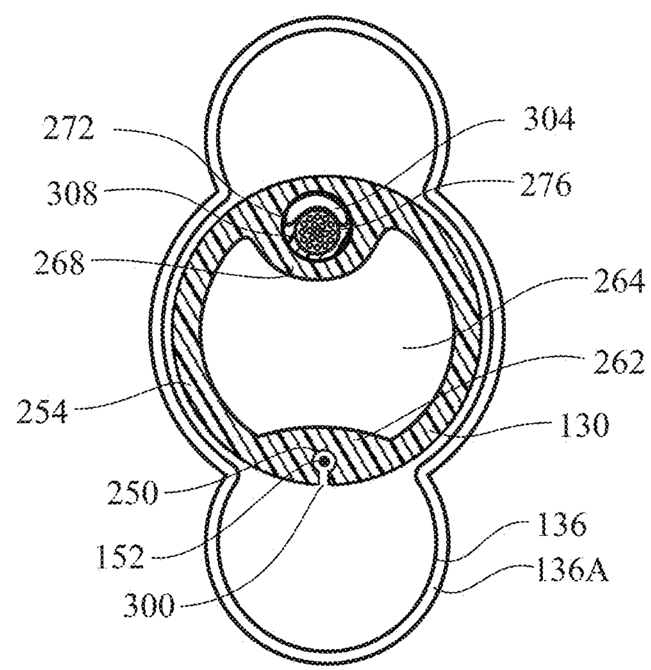
FIG. 10 shows a cross-sectional view of the feeding tube adjacent the distal end with a balloon anchor having been deployed.

FIG. 10 shows a cross-sectional view of the feeding tube 130 adjacent the distal end 130A with an anchoring device 136 with a balloon 136A anchor having been deployed. The balloon 136A is shown as being dual lobed, however it will be appreciated that numerous different designs may be used such as tri-lobed, quad-lobed hour-glass shaped, etc. The anchoring device 136 helps to hold the distal end 130A of the feeding tube 130 at the desired location in the gastrointestinal tract. (It will be appreciated that the balloon will typically be much larger relative to the feeding tube than shown in FIG. 10 when fully inflated.) It is preferred that the anchoring device 136 be multi-lobed so that it does not completely obstruct the intestinal tract, thus allowing gastric fluid to continue to move through the intestinal tract.

FIG. 10 also shows other structures at the distal end 130A of the feeding tube 130. The first lumen 250 may be used not only for the steering wire 152, but also as an inflation lumen if the anchoring device 136 is a balloon 136A. Thus, a small port 300 is provided in the first lumen 250 and extends to the exterior of the outside wall 254.

The second lumen 264 is shown as being substantially larger than the other two. As indicated above, some feeding solutions tend to be somewhat viscous. Having a larger feeding lumen is thus desirable to ensure that the feeding solution may flow through the lumen.

Figure 10A:
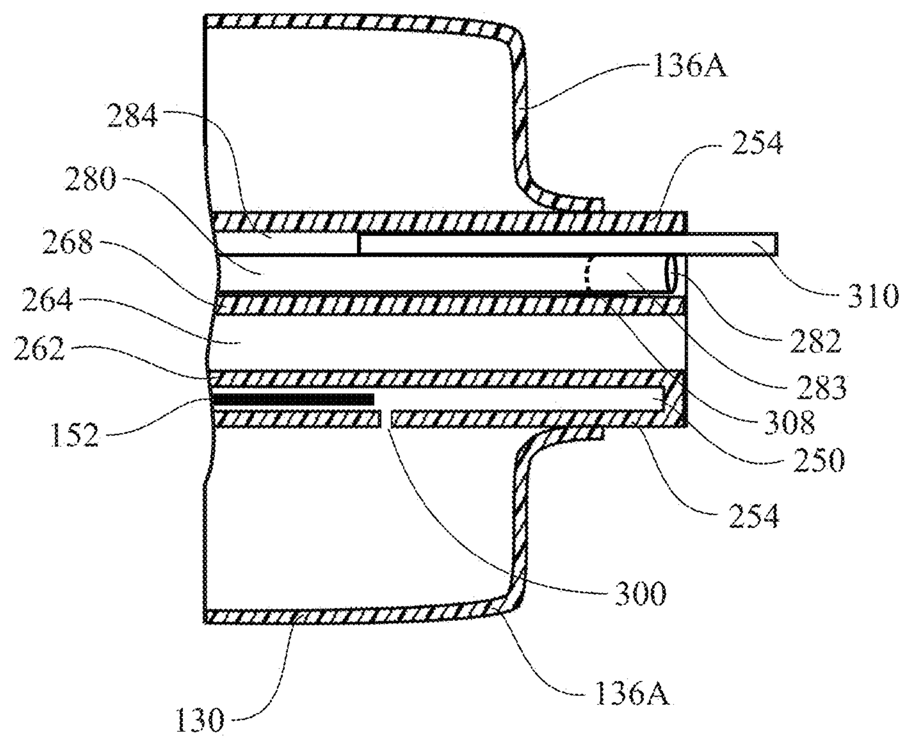
FIG. 10A shows a side cross-sectional view of the distal end of the feeding tube with a sleeve holding the distal end of the optical system in place to form a fluid flow channel within the optical system lumen.

As shown in FIG. 10, wall 268 bounds the top of the second lumen 264 and, with the outer wall 254 bounds the third lumen 272. The third lumen 272 is designed to house the optical system 276 and to provide a port 304 for fluid flow. While the optical system 276 may be left loose in the third lumen 272, it may also be anchored so that a structured port 304 is formed. This can be accomplished, as shown in FIG. 10A, by inserting a sleeve 310 into the third lumen 272 and then injecting a bonding agent 308 to hold the distal end of the optical system 276 in place. This may leave, for example, a generally crescent shaped port 304. When used with some sort of channeling mechanism, such as the deflecting projection 284, the port 304 can assist in cleaning the distal end of the optical system.

FIG. 10A shows a side-cross-sectional view at the same location as the cross-sectional view shown in FIG. 10. The various structures are numbered accordingly. An end cap, such as end cap 296, may be attached to the distal end 130A to assist in cleaning the lens 280.

Figure 11:
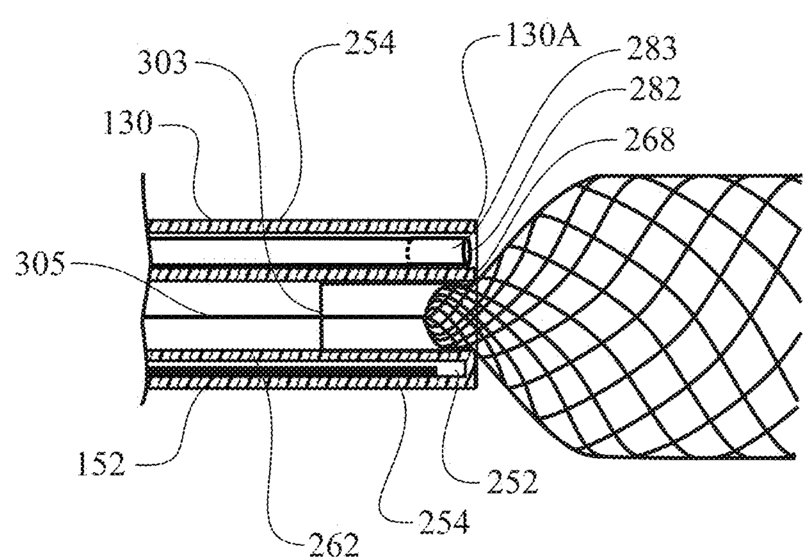
FIG. 11 shows a side cross-sectional view similar to that of FIG. 10A, but with a stent serving as the anchor.

FIG. 11 shows a side-cross sectional view of the feeding tube 130, similar to FIG. 10A. Instead of a balloon 136A for an anchoring mechanism, a stent 136*b*, such as a wall stent, is used. The stent 136B may be carried in a hypotube 303 and be connected to a wire 305. When the feeding tube 130 is properly positioned in the small bowel, the wire 305 is advanced to push the stent 136B at least partially out of the hypotube. The distal portion of the stent 136B springs open and engages the sides of the small bowel, thereby holding the feeding tube in place.

Figure 12:
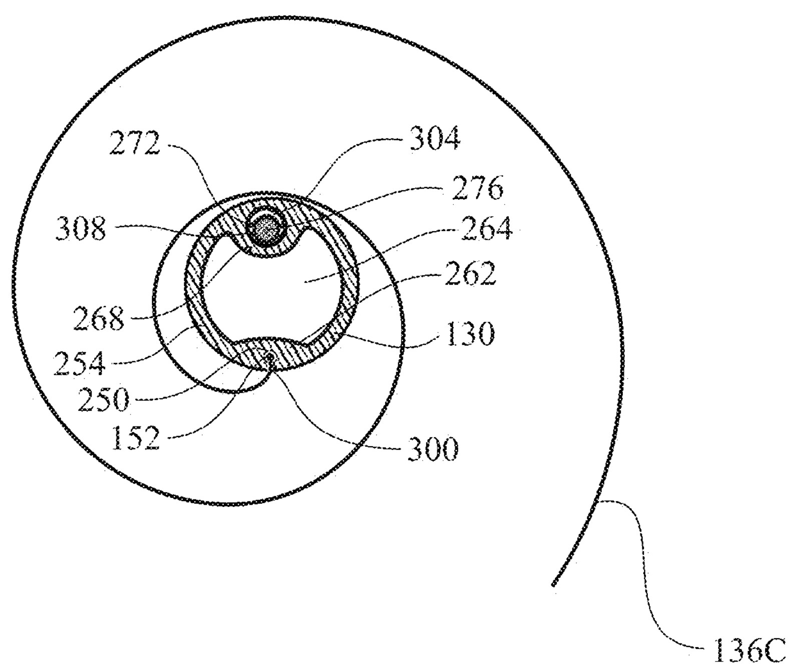
FIG. 12 shows an end view of the distal end of a feeding tube in accordance with the principles of the present invention wherein a coil 136C anchor is disposed to help anchor the distal end of the feeding tube.

Turning now to FIG. 12, there is shown an end view similar to that shown in FIG. 10. Instead of using a balloon 136A (FIG. 10) as the anchoring device 136, the anchoring device 136 is shown in the form of a helical coil 136*c*. The Stent 136 may be disposed about the exterior wall 254 of the feeding tube 130, or may be carried on the distal end 130A end of feeding tube. When the distal end 130A of the feeding tube 130 is in the desired location, the coil 136*c* stent may be activated.

Figure 12A:
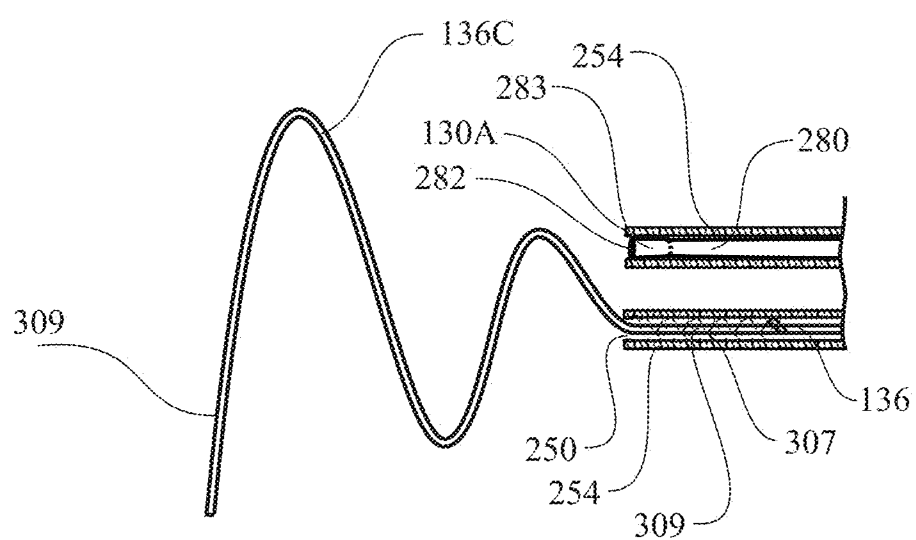
FIG. 12A shows a side cross-sectional view of the feeding tube with a coil serving as the anchor instead of a balloon or stent.

FIG. 12A shows a side view of the feeding tube 130 with the coil 136*c* deployed. During placement the coil 136*c* will typically be disposed in one of the lumens. It could be used, for example, in the lumen 250 to act as a stiffener to keep the distal end 130A of the feeding tube 130 from bending when the coil is tightly wound as shown by dashed lines 307. Moving the coil 307 proximally would allow the distal end 130A of the feeding tube 130 to curve for steering during placement. In the alternative, a stiffened section 309 could be placed distally or proximally from the coil 136. Once the distal end 130A of the feeding tube 130 is properly placed, the wire is advanced and the coil 136*c* is released, allowing it to spring open. The coil 136*c* itself may hold the distal end of the feeding tube fairly straight depending on how it engaged the intestinal wall, or stiffened portion 309*b* could be used for that purposed. While many materials could be used for the coil 136*c* a currently preferred material is nitinol.

Figure 13:
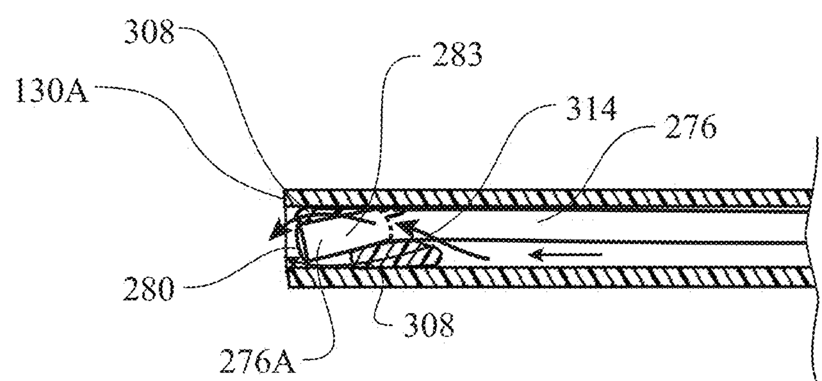
FIG. 13 shows a side cross-sectional view of an optical system/fluid lumen wherein the optical system is deflected to give a more centralized view of the tissue disposed beyond the distal end of the feeding tube.

FIG. 13 shows a side cross-sectional view of an optical system/fluid lumen 272 (the remaining lumens discussed above are omitted for clarity). The distal end 130A of the feeding tube is in contact with both the feeding solution which is gravity fed or pumped into the gastrointestinal tract and with bodily fluids such as bile, etc. To this end, and because the optical system 276 may be left in place over a prolonged period of time, it may be desirable to have the lens 280 recessed from the end of the feeding tube. This protects the lens 280. (Unlike typical endoscopes, the focusing lens 280 may be the only lens provided). While a protective lens is typically disposed at the distal end of an endoscope, such a lens could inhibit the use of the third lumen 272 both for the optical system and for solution injection to flush the lens.

Recessing the lens 280, the relative size of the feeding lumen 264, and disposal of the optical system 276 on one side of the feeding tube complicates the ability of the optical system to see the tissue adjacent the distal end 130A of the feeding tube 130 on both sides of the feeding tube. To overcome these limitations, the distal end 276A of the optical system 276 may be anchored so that the distal end of the optical system is deflected. The deflection may be anywhere from 5 degrees to 40, although 15-25 degrees toward the central long axis of the feeding tube 130 is preferred. The bonding agent 308 used to anchor the distal end 276A of the optical system 276 can be disposed both above and below the distal end 276A to obtain the proper angle, while voids are left to allow fluid flow, represented by arrows 314, around the bonding agent and over the lens 280 to clean the lens.

Figure 14:
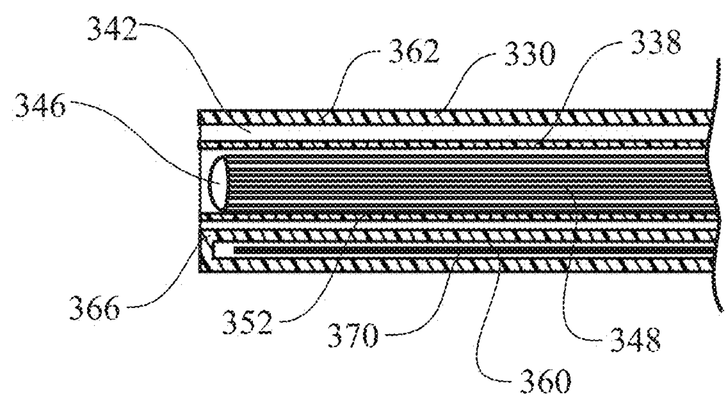
FIG. 14 shows an alternate embodiment of a feeding tube wherein the optical system is disposed in the feeding lumen for insertion or periodic observation, but which is withdrawn for feeding.

FIG. 14 shows an alternate embodiment of a feeding tube 330 made in accordance with one aspect of the present invention. Rather than have an embedded optical system 276 as discussed above, the optical system 334 is disposed in a catheter 338 which is removably disposed in a feeding lumen 342 similar to the second lumen 264 discussed above. The optical system includes a lens 346 and a plurality of optical fibers 348 surrounded by an outer wall or coating 352.

The feeding tube 330 may also include a steering lumen 360 which may be formed by an outer wall 362 of the feeding tube 330 and an inner wall 366. A steering wire 370 disposed in the steering lumen 360 can be used as described above.

The use of the feeding tube 330 is different from the use of the feeding tube 130 described above in that the optical system is removable. As the feeding tube 330 is advanced through the nasal canal, the esophagus, the stomach and the pyloric sphincter, the practitioner can view the tissues adjacent the distal end of the feeding tube on an image viewer, such as the display screen 164 of the control unit 160. Likewise, the steering wire 370 could be controlled by the control unit 160.

Once the feeding tube 330 is in place and optically confirmed, the control unit 160 can be detached and the optical system 338 can be withdrawn. With the optical system 338 withdrawn, the lumen 342 can then be used for introducing feeding solution and/or medicated solution to the patient. The optical system 338 is much less expensive than the use of an endoscope and can be either discarded or may be re-sterilized for subsequent use. If further viewing of the gastrointestinal tract is desired, the optical system 338 can be reinserted. Typically this will be done after flushing the feeding lumen 342 to clear out any feeding solution which may cloud the lens.

The feeding tube 330 is less advantageous than those discussed previously in that it does not allow viewing of the gastrointestinal tract without reinsertion of the optical system 338. However, an advantage is obtained in that the feeding tube 330 can be kept relatively small, thereby making the feeding tube 330 less discomforting to the patient and, in some situations, easier to place.

Figure 15:
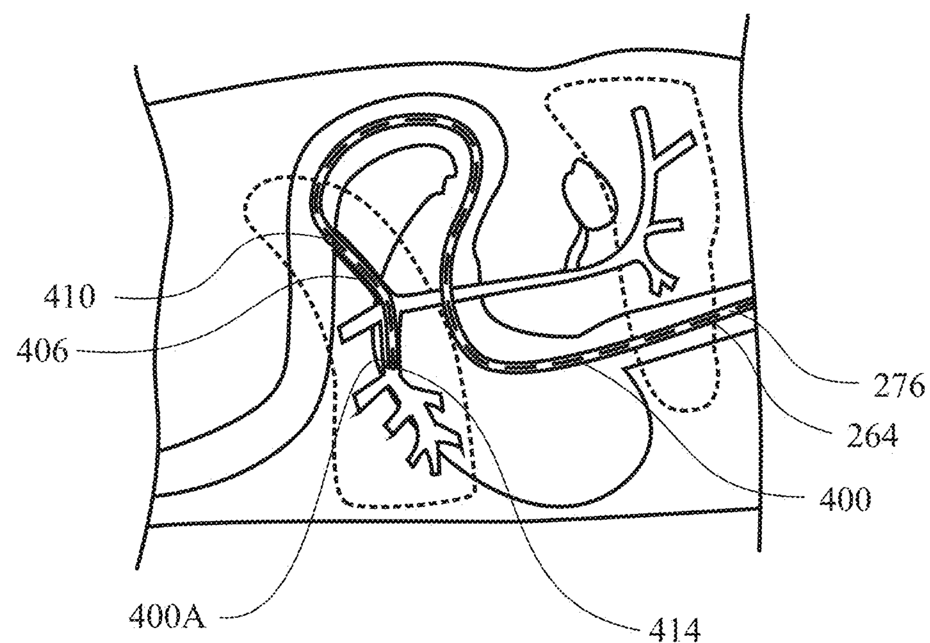
FIG. 15 shows an embodiment of a catheter having an optical system and a drainage port, with the distal end of the catheter being disposed in the pancreatic duct so as to enable visualization of the pancreas and drainage of fluids therefrom.

Turning now to FIG. 15, there is shown an embodiment of a catheter 400 in accordance with another aspect of the present invention. While not shown in FIG. 15, the catheter has an optical system formed therein, and may be structurally very similar to the feeding tube 130. The optical system enables a practitioner to view other portions of the gastrointestinal tract, such as the pancreatic duct or the common bile duct. The catheter 400 may be structurally different from the feeding tube 130 in that it may include a port 410 disposed in communication with a port 414 at the distal end of the catheter to shunt fluid through a restricted duct. The port 410 could be the proximal end of a lumen, or the lumen could extend to the proximal end of the catheter to allow the introduction or withdrawal of fluids therethrough.

When a person is suffering from pancreatitis or an inflamed common bile duct, it is common to place a stent or shunt in the pancreatic duct or the common bile duct to ensure proper drainage of bile or puss or other fluids which need to pass through the gastrointestinal tract. Typically the stent or shunt is placed, left in place for a time and then removed once the symptoms appear to subside.

The catheter 400 of the present invention allows the practitioner to use the optical system not only to place the catheter, but also to observe the tissue for a prolonged period of time. Thus, as shown in FIG. 15, the distal end 400A of the catheter is disposed in the pancreatic duct 406. Puss from an infected pancreas can pass into distal port 414 and drain through a drainage port 410 similar to a shunt. Over a period of time, the practitioner can observe the pancreatic duct to determine how well the pancreatitis is healing and can determine when assisted shunting of fluid from the pancreas is no longer needed. The same procedure could be used with the common bile duct or other structures along the gastrointestinal tract.

In use, a practitioner may insert the catheter 400 in the nasal canal of the patient. (While oral insertion can be used, one advantage of the present invention is the ability to advance through the nasal canal and avoid the complications of oral insertion). Using the optical system the practitioner can advance the catheter down the esophagus, through the stomach, through the pyloric sphincter. The catheter 400 is then turned and advanced into the pancreatic duct, the common bile duct or other structure which the practitioner needs to observe. While the catheter is left in place, the lumen between ports 414 and 410 allows gastrointestinal fluid, puss, etc. to drain. The practitioner can monitor the condition of the tissue adjacent the distal end 400A of the catheter and confirm if the patient's condition is improving. Once the catheter is no longer needed, it can be conveniently withdrawn. In contrast, a shunt or stent typically requires the reinsertion of an endoscope, or the use of fluoroscopy, etc. to withdraw the stent or shunt.

The teachings of the present invention can be applied to other fields. For example, catheters which are left in place can be provided with an optical system as disclosed. A practitioner can use the optical system to monitor internal tissue over a prolonged period of time without the need for reinsertion of an endoscope, etc.

Figure 16:
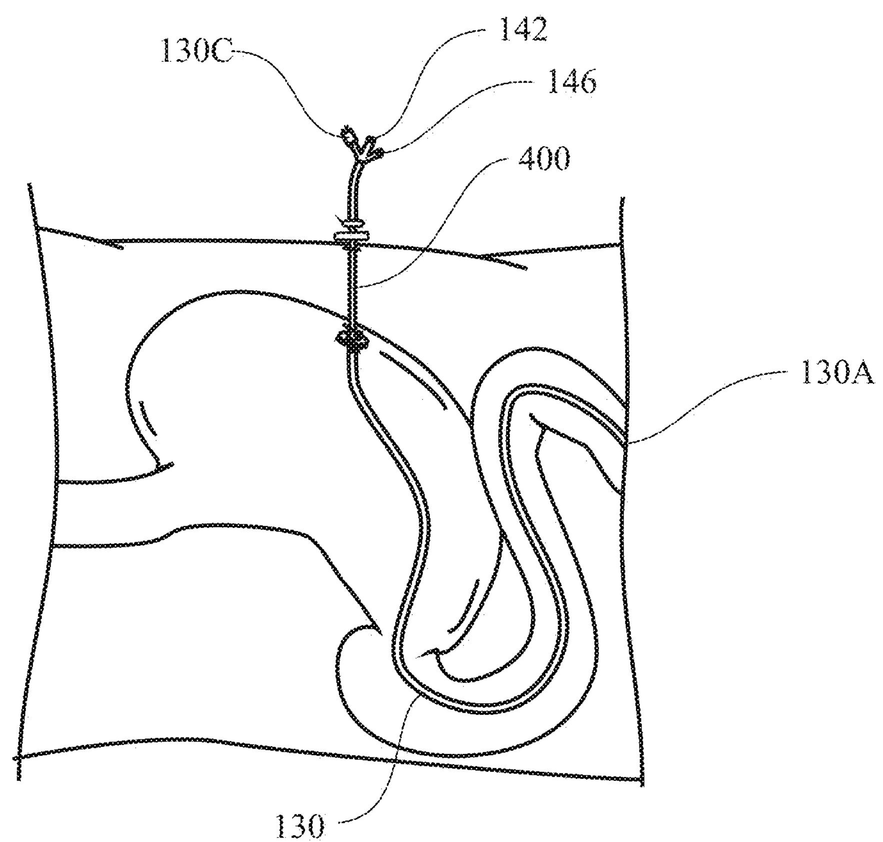
FIG. 16 shows a feeding tube formed in accordance with the principles of the present invention used as a jejunal extension tube in percutaneous gastrojejunal feeding tubes (PEGJ).

FIG. 16 shows yet another aspect of the invention. Rather than serving as a nasoenteric feeding tube, the feeding tube 130 is advanced through a percutaneous gastrojejunal feeding tube (PEGJ) to form a jejunual extension tube. Presently for PEGJ tubes the jejunal extension tube is threaded through the existing gastrostomy tube or stoma into the small bowel. This is done using fluoroscopy or endoscopy to advance a wire into the small intestine and then a jejunal feeding tube is passed over the wire into the small intestine (jejunum). In contrast, the feeding tube 130 of the present invention provides direct visualization and may include a steering mechanism could perform the same task without the drawbacks of using endoscopy or fluoroscopy as noted previously.

In use, the distal end 136A is passed through the gastostomy tube 400 in the patient's abdomen. With the control unit attached, the practitioner can observe the stomach and readily find the pyloric sphincter. The distal end 136A is advanced by pushing on the feeding tube 130 until the distal end has passed the pyloric sphincter a desired distance. An anchoring device (not shown) can then be deployed if desired help hold the feeding tube in place.

While a guidewire may be used if desired, it is generally not necessary. Additionally the cost of using an endoscope is eliminated and there is no need for confirmation of placement by use of X-ray or fluoroscopy. Additionally, the procedure of advancing the feeding tube is less time consuming and may be done by a practitioner with relatively little training.

One major advantage of the present invention is that it allows for more rapid and safer placement of a feeding tube. Additionally it avoids expensive X-rays and fluoroscopy and reduces the amount of radiation that the patient is exposed to. Another major adjacent is that it removes the need for the procedure to be done in a hospital. For example, if a patient in a nursing home has difficulty holding down food, the patient will typically be taken to a hospital where the feeding tube may be inserted—the majority being done blind. Just the time and expense of getting the patient to the hospital is disadvantageous. Additionally, the patient must undergo the procedure and be subject to radiation or other unpleasant procedures to confirm placement of the feeding tube. In the 24-48 hours that may have transpired since the patient was first diagnosed as likely needing a feeding tube, the patient may have received no food or needed medication.

A significant advance of the present invention is that placement can be done with relatively little training and need not be done in a hospital. By carefully observing the tissue, a practitioner can steer away from the trachea and ensure that the feeding tube is properly descending in the esophagus. The feeding tube can then be advanced until the practitioner is certain that the distal end of the feeding tube is a desired distance past the pyloric sphincter and then the procedure is done. The procedure may take as little as 5 to 10 minutes and could be done right at the bedside of a nursing home patient instead of at the hospital. Instead of waiting 24 hours or more for nutrition, feeding could commence in under half an hour. Additionally, there would be a substantial savings in cost and manpower by not having to transport the patient to the hospital.

Likewise, the feeding tube 130 of the present invention could be used in a variety of other situations, such as pediatric and other clinical settings or in post-operative situations where the patient is having trouble keeping down food. With a relatively short and simple procedure, nutrition can be delivered directly into the intestines of the patient. Thus, it is anticipated that substantial cost savings may be achieved at the same time making the entire procedure less straining on both the patient and the practitioner.

Figure 17:
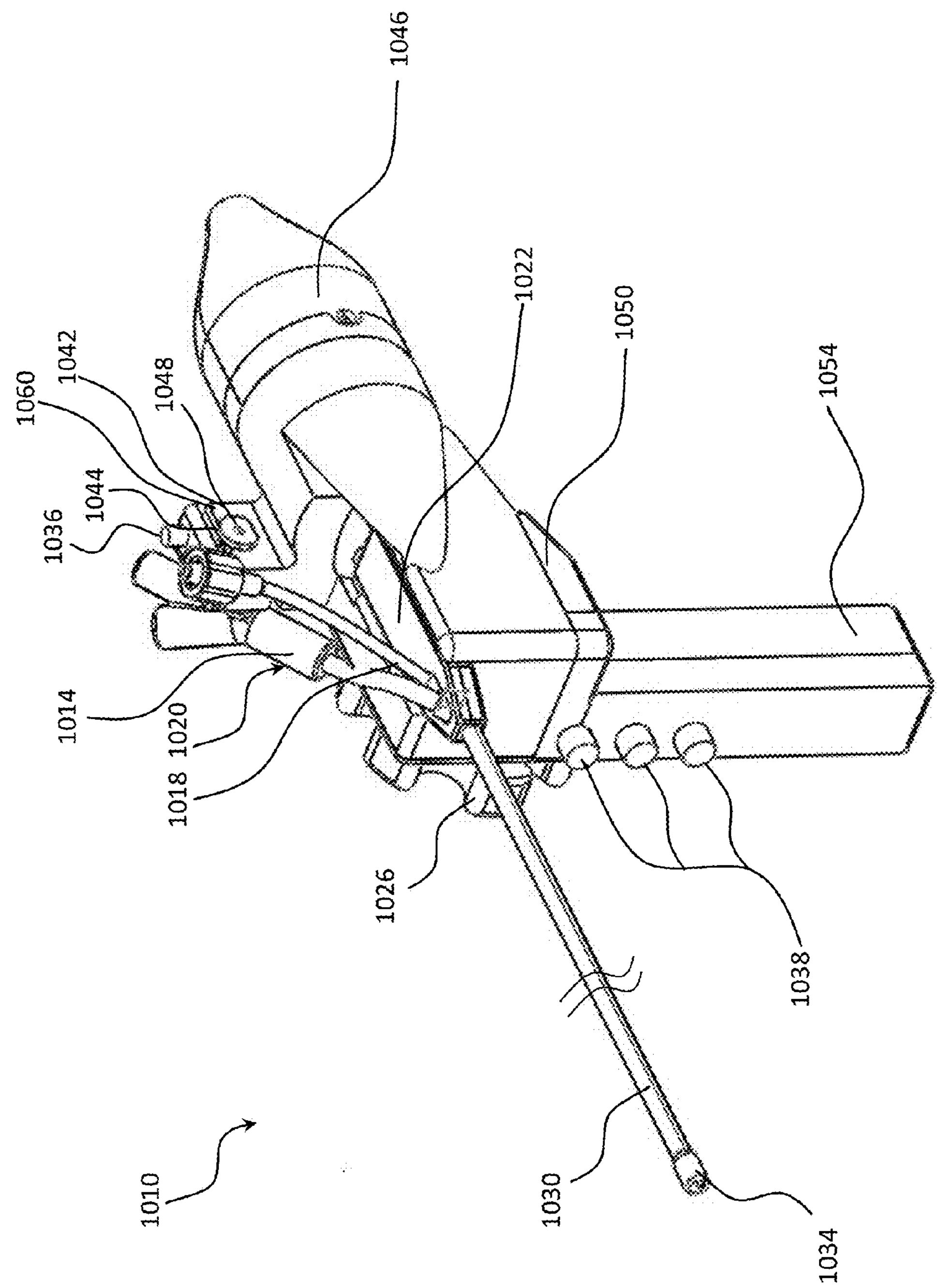
FIG. 17 shows a fragmented perspective view of an optical tube and control unit assembly made in accordance with the principles of the present invention.
Figure 18:
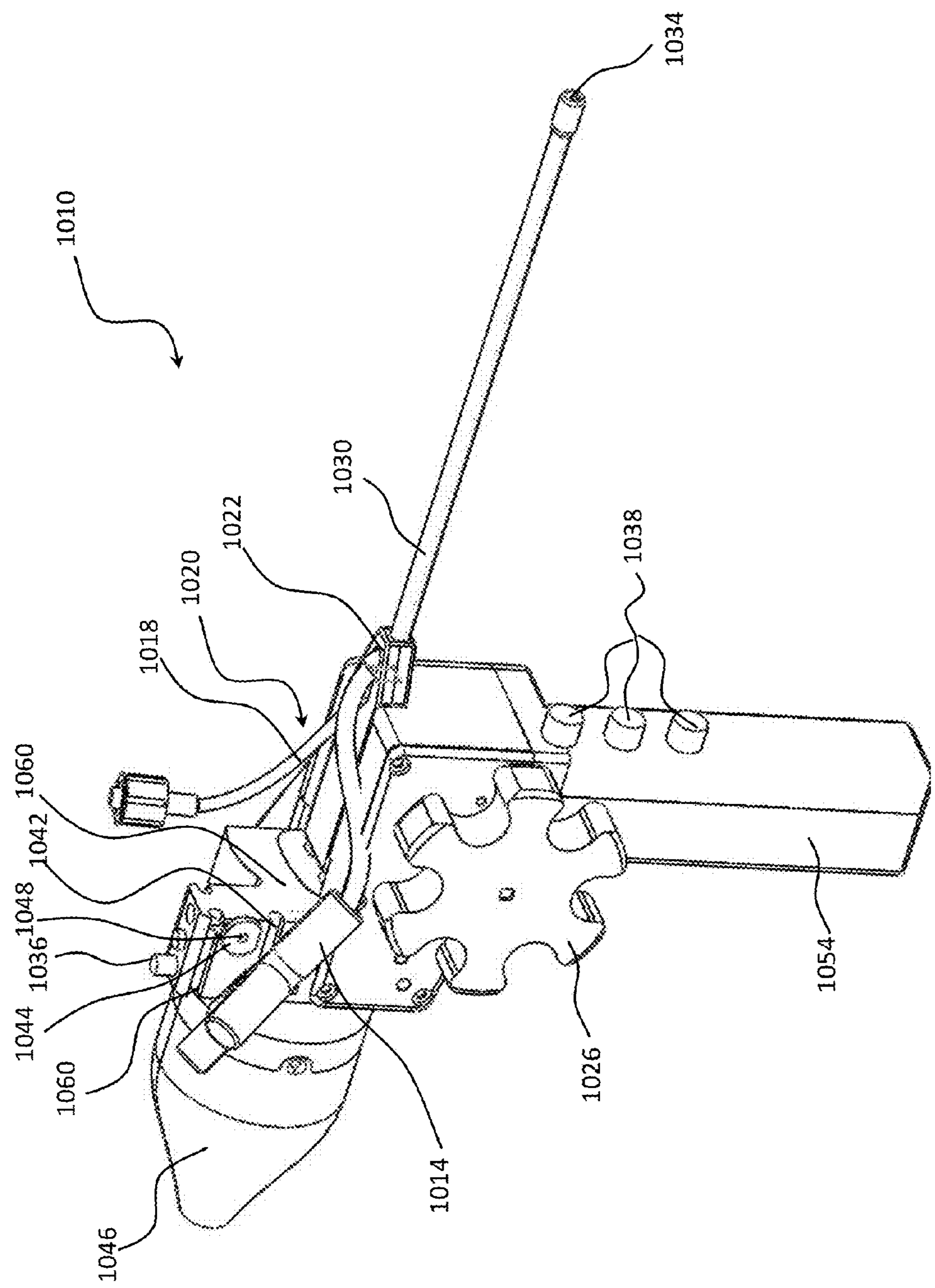
FIG. 18 shows an alternate perspective view of the optical tube and control unit assembly of FIG. 17.

Now turning to FIGS. 17 and 18, there is shown perspective views of an optical tube and control unit assembly, generally indicated at 1010, made in accordance with the principles of the present invention. The assembly 1010 may include a medical tube 1030 comprised of an imaging device 1034 and steering members (not shown), and a control unit 1050. The medical tube 1030 may be, for example, a nasoenteric feeding tube or other tube for the delivery of nutrients or other solutions to a patient. (The tube 1030 may be discussed interchangeably herein as an optical tube or medical tube as it may be used for purposes outside of a medical context if desired.)

The control unit 1050 is removably connectable to the medical tube 1030 and may include a tube mounting unit 1042, a handle 1054, a steering control, such as a thumbwheel 1026, and a housing 1046 which may contain an image capturing device and/or light source. One advantage of one aspect of the present invention is that the control unit may be used independent of a given medical tube 1030. Thus, for example, a physician may carry a control unit and use the unit with multiple medical tubes disposed in a number of patients without the need to sterilize the control unit 1050.

When the medical tube 1030 is coupled to the control unit 1050 the imaging device 1034, such as an optical fiber, may be aligned so as to allow light from a light source located in housing 1046 to be directed through the optical fiber 1034 to a distal end of the medical tube 1030 to thereby provide light as the medical tube 1030 is advanced along a pathway. Additionally, the imaging device 1034 may be aligned so as to transmit information to the imaging capture device which may be located in housing 1046, thus allowing the user of the assembly 1010 to view an area when direct line-of-sight observation would otherwise be difficult or impossible. For example, medical personnel using the assembly 1010 would be able to visually navigate a tube 1030 down the nose, through the esophagus and into the stomach or small intestine, in order to place a feeding tube for treatment of a patient. By providing the medical personnel the ability to see as he or she advances the tube 1030, assembly 1010 may reduce the risk that the patient will be injured during the placement procedure, decrease the time necessary to place the tube, and allow for immediate confirmation that the tube 1030 is properly placed. Thus, the risk of a cranial or lung injury to a patient may be dramatically reduced and the time and expense of confirming proper placement may be reduced from hours to minutes.

The optical tube and control unit assembly 1010 may also include a steering mechanism to facilitate navigation of the tube 1030 through a tortuous pathway. The steering mechanism (which is explained in more detail below) may include the medical tube 1030 having one or more wires which are operationally connectable to the control unit and which may be used to steer the tubing 1030 using a steering control such as, for example, thumbwheel 1026, a wheel, lever, etc.

As can be seen in FIGS. 17 and 18, tube 1030 may be coupled (either permanently or temporarily) to a coupling adaptor 1022, which is configured for removably connecting to the control unit 1050. The coupling adaptor 1022 may allow quick and simple engagement of the steering mechanism with the control unit 1050 and alignment of the imaging device 1034 with the image capturing device and light source in housing 1046. As explained in further detail below, engagement of the steering mechanism and alignment of the imaging device may occur simultaneously upon placement of coupling adaptor 1022 in or on the control unit 1050, such as in a recess. Once the medical tube 1030 is guided to its proper location, coupling adaptor 1022 can be disconnected from control unit 1050, enabling the control unit to be used with other medical tubes. Because the control unit 1050 may not come into direct contact with the body, the control unit 1050 may be cleaned by simply wiping it with an antiseptic wipe rather than requiring a more complex sterilization procedure. This will likely reduce both time and expense for medical personnel and the patient.

Coupling adaptor 1022 may be constructed so as to be lightweight and small enough to go substantially unnoticed when the medical tube 1030 is intended to be associated with a patient for a prolonged period of time. Thus, the coupling adaptor 1022 may remain on the medical tube 1030 with minimal, if any, disturbance of the patient. Medical personnel may easily reconnect the coupling adaptor 1022 to the control unit 1050 at a later time in order to confirm that the medical tube 1030 has not been inadvertently displaced, to view tissue surrounding the distal end of the medical tube, to change position of the medical tube, or perform other acts or procedures as is necessary.

It will be appreciated that the ability to easily engage and disengage the coupling adaptor 1022 from the control unit 1050 to thereby allow both the optical components and steering mechanisms of the medical tube 1030 to be utilized multiple times has several advantages over devices traditionally used to view inside the body, namely endoscopes. In particular, the assembly 1010 may be used multiple times without the need for time consuming and expensive procedures to sterilize the assembly. In contrast, an endoscope must be properly prepared and sterilized prior to reuse in order to reduce the risk that an infection could be transmitted from one patient to another. Furthermore, the patient need not be subjected to additional procedures in order to confirm that the medical tube 1030 has not been displaced. Medical personnel need only reconnect the coupling adaptor 1022 to the control unit 1050 in order to confirm that the tubing is in its proper place and, if not, re-advance the tubing to the position where it should be located.

An additional aspect of the optical medical tube and control unit assembly 1010 that can be seen in FIGS. 17 and 18 is a tube mounting unit 1042. The tube mounting unit 1042 may be used to couple tubing to the control unit 1050 and provide the ability of medical personnel to control flushing, aspiration and/or insufflation during use of the assembly 1010, which is described in more detail below. To give a brief example, the tube mounting unit 1042 may have one or more retention members 1044 for selectively holding tubing segments in place and one or more occlusion members 1048 for selectively controlling the flow of fluid from an external source through a lumen in the medical tube 1030. (It will be appreciated that the medical tube 1030 may have more than one lumen). Control of the retention members 1044 may be provided by one or more retention buttons 1036 or other retention control members to selectively allow placement or removal of a tubing segment from a retention location 1060, such as a channel, void, space, etc., in the tubing mounting unit 1042.

Likewise, buttons or flow control members 1038, which may be disposed along a handle portion 1054 of the control unit 1050 may enable control of flow through the tubing segments (not shown in FIGS. 17 and 18) disposed in the channel(s) 1060. This may be done, for example, by being biased into a position wherein an occlusion member 1048 pinches closed a tubing segment. Applying a force to a button 1038, which may be operatively connected to the tube mounting unit 1042 and an occlusion member 1048, may move the occlusion member from a first, closed position to a second, open position, wherein it no longer applies sufficient force to the tubing segment to pinch the tubing segment closed. Releasing force on the button 1038 may allow the occlusion member 1048 to return under bias to the first, closed position. By selectively pushing buttons 1038, medical personnel are able to control fluid flow into a lumen in the medical tube 1030 and selectively control which fluids are allowed to pass through the tubing segments into the medical tube (or the creation of a vacuum within the medical tube due to a vacuum in a connected tubing segment). (It will be appreciated that the function of buttons 1036 and 1038 could be combined to provide a single control button which enables mounting and removal of the tubing, along with selective occluding of flow through the tubing.)

Tubing mounting unit 1042 may comprise a plurality of locations for engaging a plurality of tubing sections to thereby provide for multiple functionalities, such as flushing of the optical fiber at the distal end of the medical tube 1030, aspiration of a fluid from the body of the patient, etc. These locations may be channels 1060 formed in the tube mounting unit 1042 or the interaction of the retention members 1044 and the body of the tube mounting unit 1042 to adequately secure the tubing segments.

The optical medical tube and control unit assembly 1010 may also include a tube adaptor 1020 for operatively connecting the medical tube 1030 to a separate tubing section (see e.g. FIG. 29A) designed to be received by the tube mounting unit 1042. The tube adaptor 1020 may include a first section 1014 in fluid communication with a lumen of the medical tube 1030 configured to deliver medicine, nutrients and/or other solutions to a patient after placement of the medical tube 1030, or configured to provide aspiration and insufflation during or after placement of the medical tube 1030. The tube adaptor 1020 may also include a second section 1018 in fluid communication with a lumen of the medical tube 1030 configured to provide a way to flush the imaging device 1034 at the distal end of the medical tube 1030 to enable better image capture by the assembly 1010.

As was mentioned previously, the control unit 1050 may include an image capturing device and/or light source to enable viewing through the imaging device 1034. Thus, the housing 1046 may include a video screen (not shown) or a connector for attaching the housing to a viewing screen such as a monitor, a smart phone or other visual display to enable a physician or other medical personnel to view the tissue adjacent the distal end of the imaging device.

It will be appreciated that, although the discussion may be focused on optical tubes intended for use in the field of medicine, and more specifically optically guided feeding tubes, optical tube systems may have many uses in situations when there is a need to inspect an area that is inaccessible by other means. For example, optical tube systems are used to inspect large engines or turbines, have forensic applications in law enforcement, can be used in gunsmithing for inspecting the interior bore of a firearm, and are used by bomb disposal personnel to examine improvised explosive devices. Optical tube systems have even found use in architectural work as a way to visualize scale models of proposed buildings.

Figure 19:
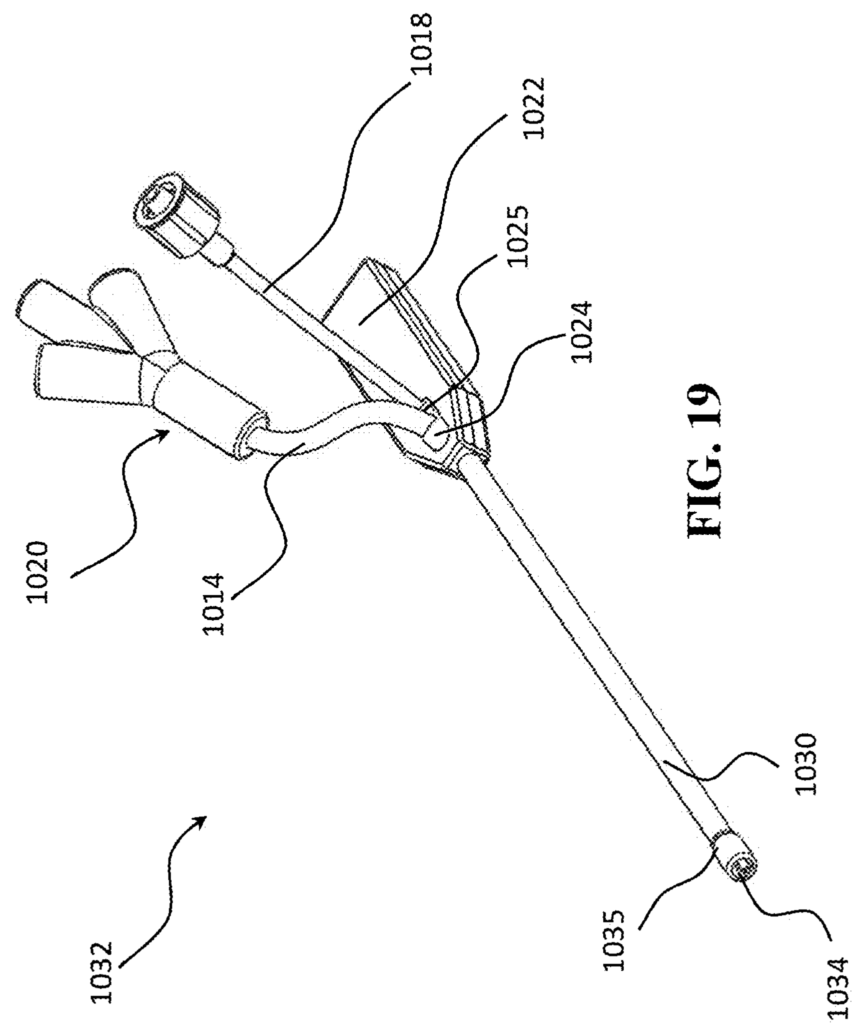
FIG. 19 shows a fragmented perspective view of an optical medical tube and coupling adaptor of the present invention.

Turning now to FIG. 19, there is shown a fragmented perspective view of an optical medical tube, generally indicated at 1030 and coupling adaptor 1022 forming an optical medical tube assembly, generally indicated at 1032. Optical medical tube assembly 1032 may include a medical tube 1030 having multiple lumens, including lumens for an imaging device 1034. The imaging device may comprise an optical fiber with a light ring or a camera on a wire including a light source. The optical medical tube assembly 1032 may also include a steering mechanism associated therewith. The tube 1030 may also include a lumen configured to deliver medication, nutrients and/or other solutions post-placement of tube 1030, lumens designed to flush the imaging device 1034, and steering members (not shown in FIG. 19).

In addition, optical medical tube 1030 may include a tube tip 1035 disposed so as to align the imaging device 1034 generally parallel with the center axis of tube 1030 which may facilitate transmission of a view at the distal end of the tip 1035 to the user of the assembly 1010. The tube tip 1035 may also help direct flushing of the imaging device 1034 and may provide an anchor point for the steering mechanism.

The medical tube 1030 may be coupled to a coupling adaptor 1022, which may be configured to be removably connected to a control unit 1050 of the assembly 1010. Coupling the tube 1030 to a coupling adaptor 1022 that is small and lightweight may be advantageous in that the coupling adaptor 1022 may go substantially unnoticed to the patient in which the tube 1030 has been placed increasing patient comfort while allowing the control unit 1050 to be quickly and easily reconnected to and/or disconnected from the tube 1030 at a later time.

The optical medical tube assembly 1032 may also include a tube adaptor 1020. The tube adaptor 1020 may include a connector 1014 for connecting to devices configured for administering medicine, nutrients or other solutions after the tube 1030 has been placed. As an example, the connector 1014 may connect to devices configured for delivering a fluid for flushing or insufflation and also to devices configured for providing suction capabilities for aspirating a fluid from the body. Additionally, the tube adaptor 1020 may include a flush port 1018 for flushing the imaging device 1034. The flush port 1018 may be capped after placement of tubing 1030 unless reconfirmation that the tube 1030 is in its proper place is later needed.

Both the tube adaptor 1020 and the flush port 1018 may connect to the tube 1030 via the coupling adaptor 1022 in a manner that eliminates cross communication between lumens associated with the optical medical tube 1030. The coupling adaptor 1022 may have one or more channels therein configured so as to communicate with a specific lumen in the tube 1030. For example, the connector 1014 may be attached to a coupling adaptor 1022 at one end 1024 of a channel in the coupling adaptor 1022 so that if a fluid is introduced into connector 1014 it passes through the channel and only into a lumen configured for administration of medication, nutrients and/or other solutions. A second channel may exist in the coupling adaptor 1022 at the location where the flush port 1018 connects to the coupling adaptor 1022, such that the second channel only communicates with a lumen configured for flushing of the imaging device 1034.

Figure 20:
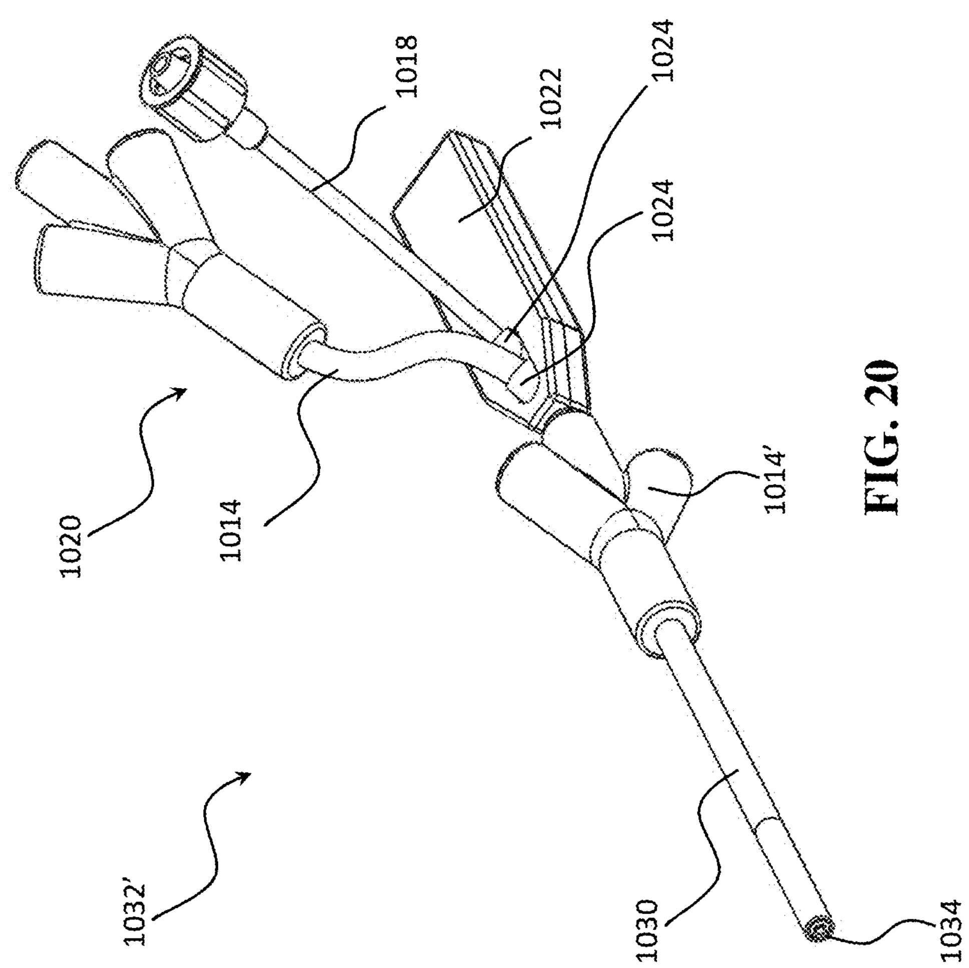
FIG. 20 shows a fragmented perspective view of another optical medical tube and coupling adaptor of the present invention.
Figure 21:
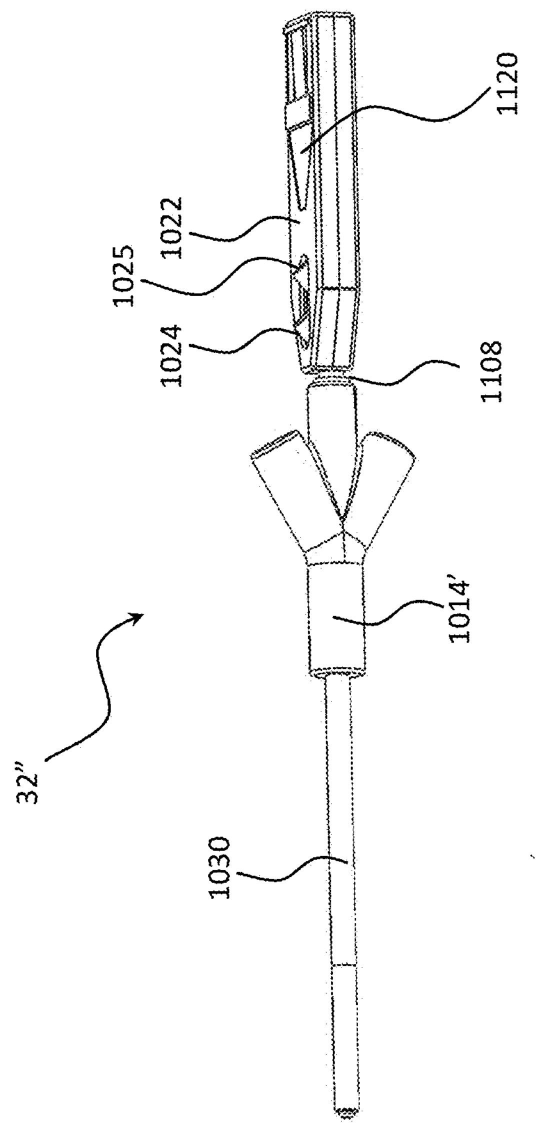
FIG. 21 shows a fragmented perspective view of yet another optical medical tube of the present invention.

Turning to FIGS. 20 and 21, there are shown perspective views of additional aspects of optical medical tube assemblies according to principles of the present invention, generally indicated at 1032' and 1032" respectively. The assemblies 1032' and 1032" may include a second connector 1014'. Connector 1014' may be disconnected from coupling adaptor 1022 post-placement of a tube 1030 and be used to connect to devices configured for administering medication, nutrients and/or other fluids to a patient. Assemblies 1032' and 1032" may also include connector 1014 (not shown in FIG. 21) for connecting to a tubing section loaded on the tube mounting unit shown in FIG. 17 to provide the user of an assembly 1010 various functionalities during placement of the tube 1030.

Figure 24:
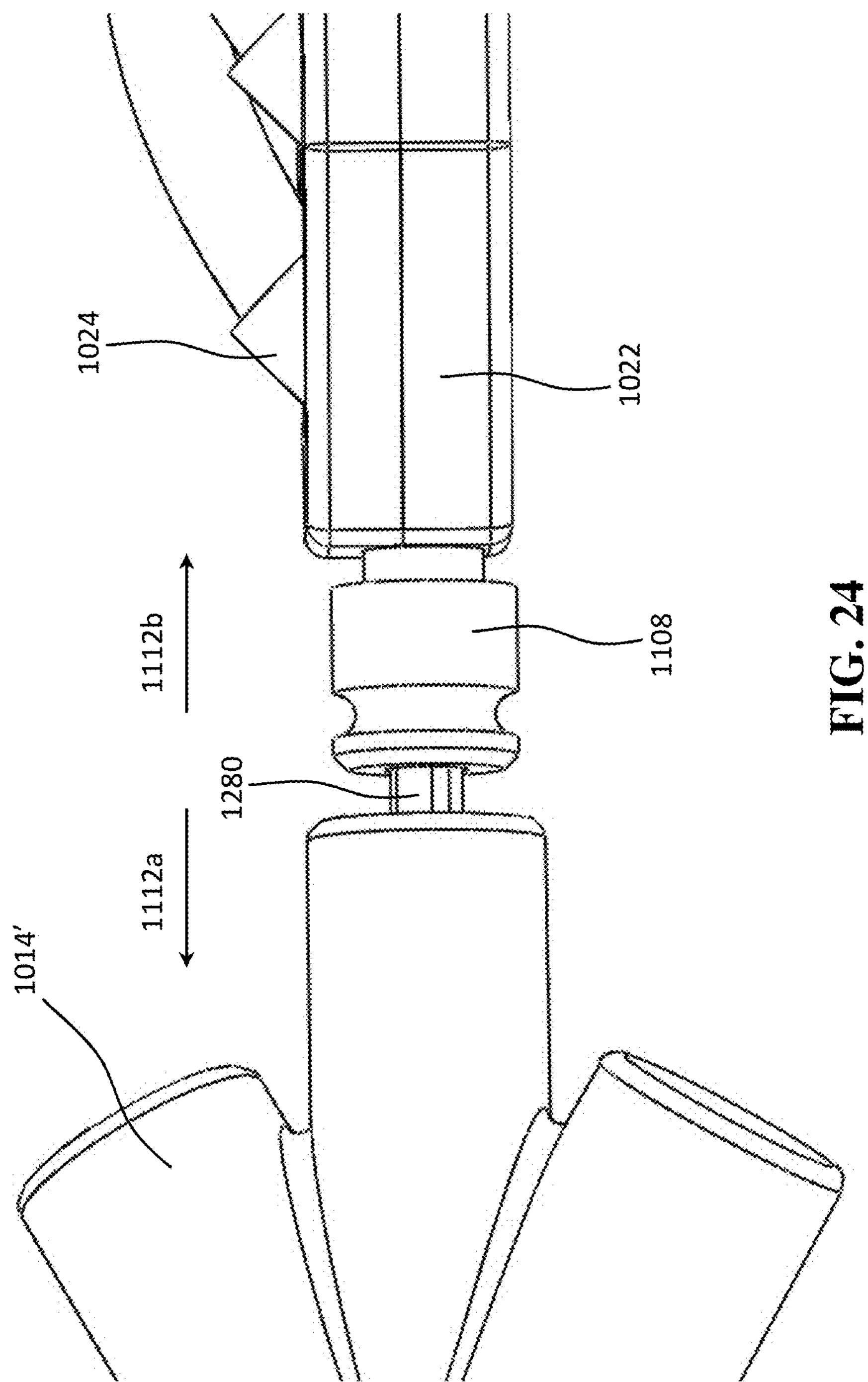
FIG. 24 show a close-up perspective view of an optical medical tube with a connector associated therewith being disconnected from a coupling adaptor.

The coupling adaptor 1022 may be detached from the tube 1030 after placement at a connection point 1108 (FIG. 21) between the connector 1014' and the coupling adaptor 1022, as can be seen better in FIG. 24. It will be appreciated that there are various methods for connecting connector 1014' to coupling adaptor 1022 including use of a twist lock, luer lock, bayonet lock, barbed fitting, O-ring fittings, and the like. When the tube 1030 is intended to be left in a patient for an extended period of time, detachment of the coupling adaptor 1022 may be desirable so that the patient is as comfortable as possible. If confirmation that the tube is in its proper place is later needed, it is simple to attach a new coupling adaptor 1022 to the tube 1030 in order to have the ability to view and steer the tube 1030 if necessary.

An additional aspect that can be seen in FIG. 21, is the coupling adaptor 1022 having an optical fiber connector 1120. The optical fiber connector 1120 may have a snap-fit connection to the coupling adaptor 1022 and provide for removal of the optical fiber from the tube 1030. Thus allowing for reuse of the optical fiber following simple cleaning, such as swabbing the optical fiber with an alcohol swab. The ability to remove and reuse the optical fiber may be advantageous because typically the optical fiber which needs to be used with an optical medical tube assembly 1032, 1032', or 1032" can be expensive. For example, the optical fiber may need to have a sufficiently small enough outer diameter to allow a tube to be comfortably advanced through a narrow passageway while maintaining enough space in the tube for additional lumens and structures for various functionalities. Such optical fibers usually have to be made from more expensive materials because image quality from optical fibers made of cheaper materials is too poor for the intended purposes of the present invention. Thus, the ability to remove and reuse an optical fiber may be important to make the optical feeding tubes of the present invention cost effective by allowing less expensive, larger optical fibers to be used.

Figure 22:
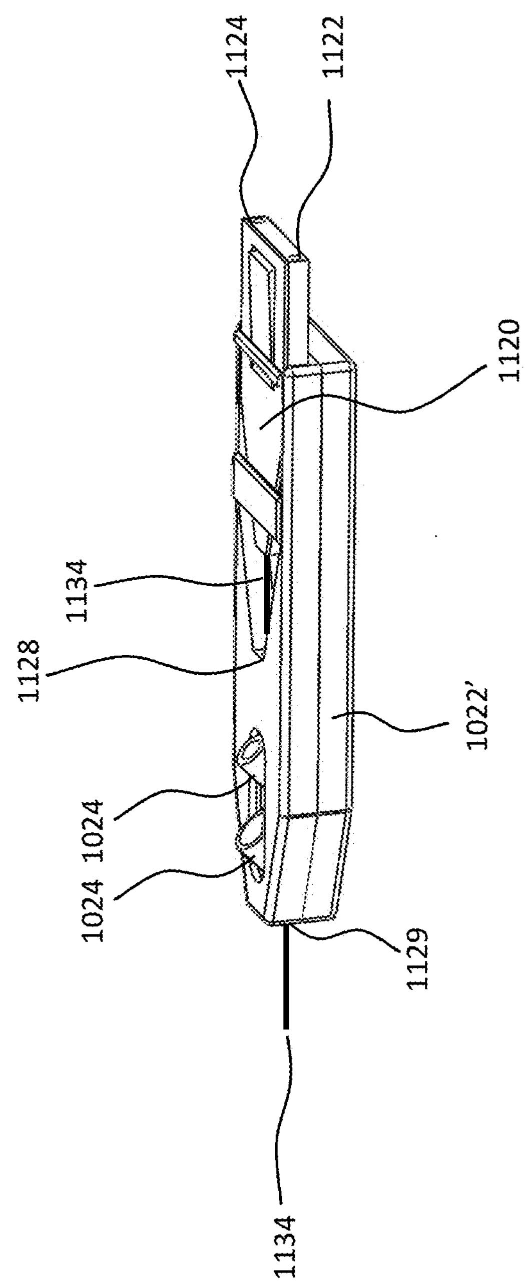
FIG. 22 shows a perspective view of the coupling adaptor of the optical medical tube in FIG. 5.

An example of how an optical fiber 1134 is removed from or attached to a coupling adaptor 1022 can be better seen in FIG. 22. The optical fiber 1134 may be removably attached to the connector 1120. The optical fiber 1134 may include a one or more fibers for transmitting light down a medical tube, and one or more fibers associated with an image capture device.

The connector 1120 have a releasable connection (e.g. a snap fit connector) with coupling adaptor 1022 in a manner that provides for the optical fiber 1134 aligning with both a light source at position 1124 and an image capturing device at position 1122. The optical fiber 1134 may be directed to a lumen in a tube 1030 (not shown) via a channel in coupling adaptor 122 that may run from an insertion point 1128 to an exit point 1129. When a tube 1030 is coupled to the coupling adaptor 1022, the optical fiber 1134 may be aligned to enter a lumen in the tube 1030 (or a stylet, which is describe in more detail below) when exiting the coupling adaptor 1022 at exit point 1129. By disconnecting the connector 1120 from adaptor 1022', the optical fiber 1134 can be slid out of the adaptor after use and then sterilized or cleaned for reuse when needed. Even if the optical fiber 1134 is sterilized prior to use on another patient, resterilizing the optical fiber is less expensive and time consuming that resterilizing an endoscope.

Figures 23A, 23B:
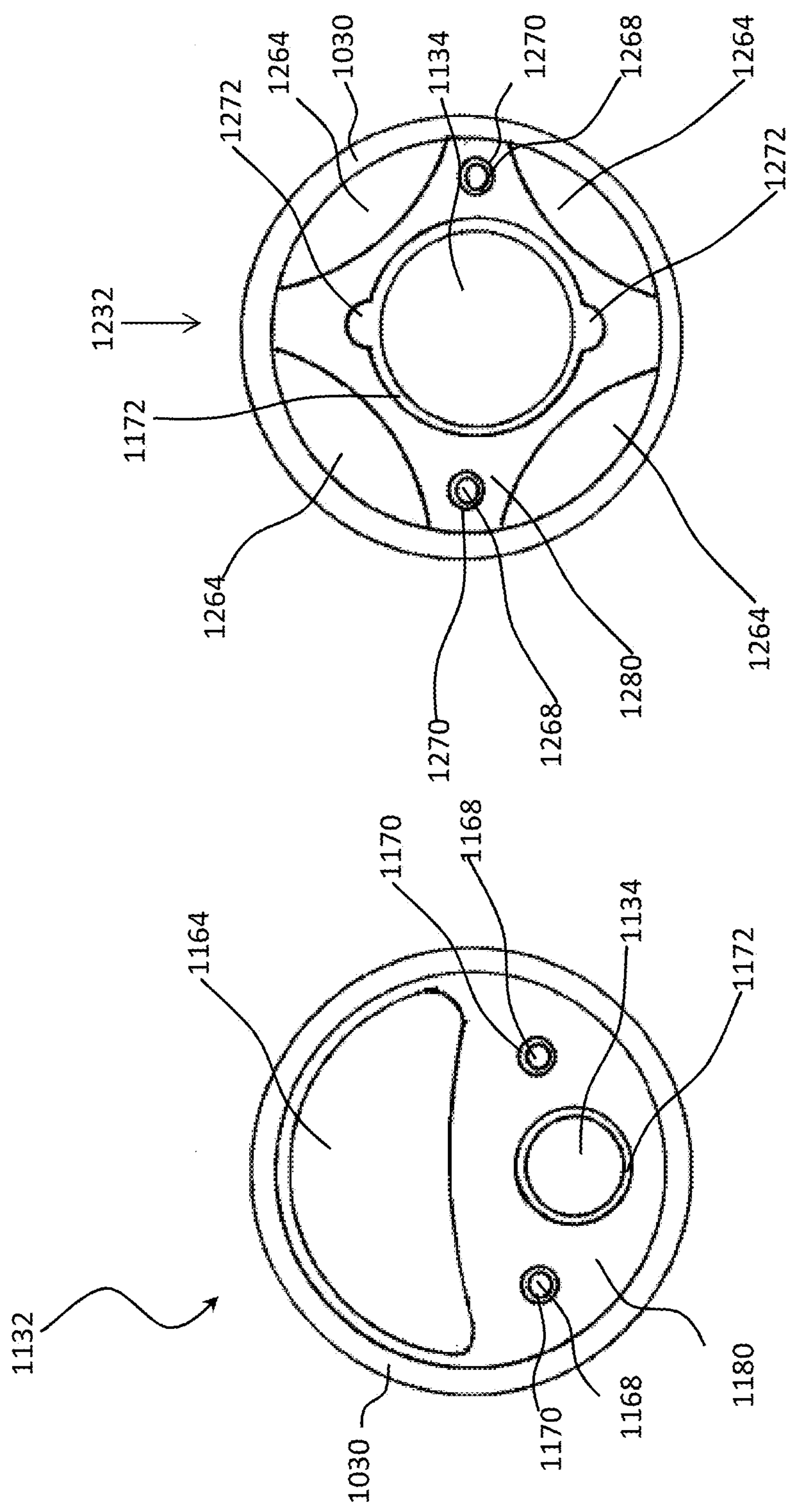
FIG. 23A shows an end view of a tube of an optical medical tube made according to principles of the present invention.
FIG. 23B shows an end view of another tube and stylet of an optical medical tube made according to principles of the present invention.

Turning to FIG. 23A, there is shown an end view of a medical tube 1030 of an optical medical tube assembly, generally indicated at 1132, made according to principles of the present invention. The tube 1030 includes a lumen 1164 that may be used for flushing, insufflations, or aspiration during or after placement of the tubing, or may be used for delivering medication, nutrients and/or other fluids to a patient post-placement. The tube 1030 may include a lumen for an imaging device 1134, such as an optical fiber. Substantially adjacent or surrounding the imaging device 1134 may be a lumen 1172 connected to the flush port 1018 (see e.g. FIG. 19). The lumen 1172 may be used to flush the imaging device to provide the user of an assembly 1010 with higher quality images for placing the tube 1030 or for confirming that tube 1030 has not been inadvertently displaced after it has been inside the patient over a period of time. As can be seen in FIG. 23A, the tube 1030 may be configured to substantially prevent cross communication between lumens 1172 and 1164.

The tube 1030 may also include multiple lumens 1170 for receiving steering members 1168, such as steering wires. Use of multiple steering wires 1168 may provide for multidirectional deflection of the optical medical tube 1132 during placement. One skilled in the art will appreciate that steering wires 1168 may be strings, lines, cables and the like so long as what is used can adequately deflect the tube 1030 so that a user of assembly 1010 may follow the pathway of a structure under examination, with minimum deflection or friction force upon the surrounding tissue, and to survey targeted examination sites.

As is explained in further detail below, the optical medical tube assembly 1132 may include a tube tip (FIG. 31) to provide alignment for imaging at the distal end of the tube 1030. The tip may also aid in facilitating flow of fluids, nutrients and medication from lumens 1164 and 1172.

FIG. 23B, shows a front view of a tube 1030 and a stylet 1280 that may be used with an optical medical tube assembly, generally indicated at 1232, of the present invention. The stylet 1280 may include or, with the tube, define multiple lumens that perform substantially the same functions as described above. However, the generally X-shaped cross-section of the stylet 1280 may provide additional advantages. For example, the X-shaped configuration may allow the stylet 1280 to receive an imaging device such as optical fiber 1034, having a larger outer diameter than can be received by the lumen 1172 of the tube 1130 in FIG. 23A. This enables the use of less expensive optical fibers manufactured using, for example, plastic, which have a greater outer diameter (approximately 1.8 mm to 2.0 mm) to provide comparable image quality to the more expensive smaller fibers.

The lumens 1264 in the medical tube 1230 may perform substantially the same functions as lumen 1164 in FIG. 23A. The lumens 1264 may be formed by the inner surface of the tube 1230 and various surfaces of the stylet. The stylet 1280 may also include lumens or channels 1272, which may be located substantially adjacent to the imaging device 1134 so as to provide for flushing of the imaging device when needed, and lumens 1270 for receiving steering wires 1268. As will be discussed in further detail below, the generally X-shaped cross-section of the stylet 1280 may provide the added advantage of increasing control of the movement of the tube 1230 at the distal end.

FIG. 24 shows a close-up perspective view of an optical medical tube similar to that shown in FIG. 21, with a connecting point or member 1108 disposed between the connector 1014' and the coupling adaptor 1022. This could be used, for example, with a stylet 1280 so that the coupling adaptor 1022 can be disconnected from the connector 1014' and the stylet 1280 can be pulled out of the tube 30 when it is not needed. The remaining medical tube 1030 can be used for feeding, and administering medications, etc., and the stylet 1280 may be reinserted if desired for confirming tube placement, etc.

Figure 25A:
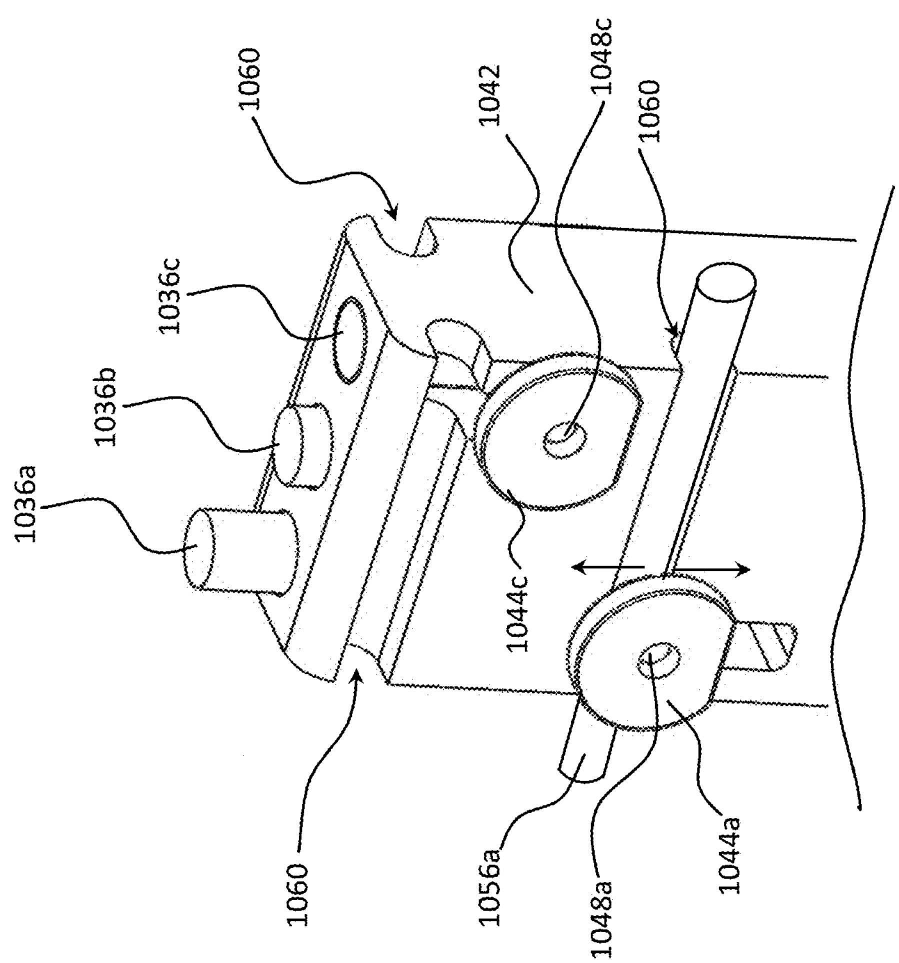
FIG. 25A shows a perspective view of a tube mounting unit and a tubing segment according to one aspect of the present invention.
Figure 25B:
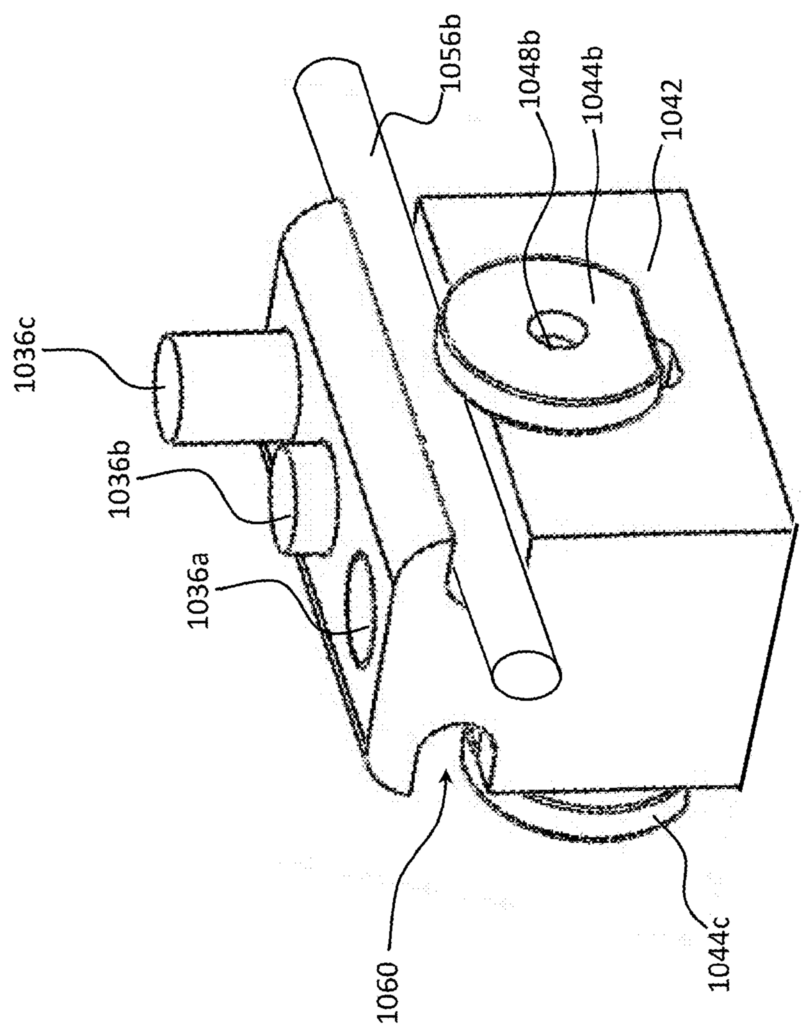
FIG. 25B shows an alternate perspective view of the tube mounting unit of FIG. 25A having a tubing segment in a different channel.

Turning now to FIGS. 25A and 25B, there are shown close-up, perspective views of a tube mounting unit 1042 which may form part of the control unit 1050. The tube mounting unit 1042 may comprise one or more retention locations 1060, such as channels, for engaging tubing sections according to principles of the present invention (such as a disposable tubing section described below). The tube mounting unit 1042 may also comprise one or more retention members, such as retention members **1044*a*-1044*c*, located adjacent channels 1060 for holding tubing sections in channels 1060 during use. It will be appreciated that the one or more retention members 1044*a*-1044*c* could be configured with a channel or other structure to hold the tubing segments without the need for channels 1060** in the tube mounting unit.

As shown in FIGS. 25A and 25B, the retention members **1044*a*-1044*c* may be generally disc shaped and configured so that a portion of the retention member may be disposed alongside the tubing segment 1056*a* to hold the tubing segment in place. Thus, the retention members 1044*a*-1044*c*** may be selectively moveable between at least two positions, open or loading and closed or retaining, and can potentially be disposed in at least three or more positions.

According to one aspect of the invention, the retention members **1044*a*-1044*c* are typically biased in a closed position by a biasing member, such as a spring, elastomeric material, etc. (not shown). In the embodiment shown in FIGS. 25A and 25B, the retention members 1044***a*-1044*c* are connected to a biasing member disposed in the tube mounting unit 1042 by a shaft, bar, etc. 1048*a*-1048*c*. As will be explained below, the shaft, bar, etc. 1048*a*-1048*c* may also serve as an occlusion member 1048 for selectively terminating flow through a tubing segment 1056*a* disposed in one of the channels 1060 by, for example, pinching the tubing segment to selectively prevent flow therethrough.

Figure 25C:
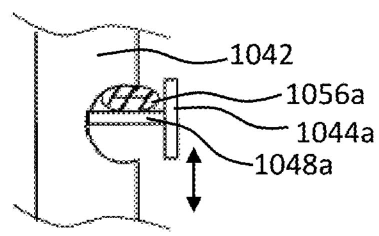
FIG. 25C shows a close-up view of an occlusion member and retention member occluding a tubing segment as shown in FIG. 9A.

The retention member 1044*a* is shown biased into a first, closed position. (A close-up view is shown in FIG. 25C). The retention member 1044*a* is disposed alongside the channel 1060 to prevent the tubing segment 1056*a* from being withdrawn from the channel. As shown, the occlusion member 1048*a* is advanced upwardly to an extent where it will pinch closed the tubing segment and prevent fluid flow therethrough. Such a position would typically be associated with one of the buttons 1036*a* or 1038*a* (FIG. 26) being left undepressed. In this position, the retention member 1044*a* holds the tubing segment 1056*a* in place in the channel 1060 and the occlusion member 1048*a* substantially prevents flow therethrough. The retention member 1044*a* and the occlusion member 1048*a* may also be moved into additional positions as discussed below with respect to the other retention members 1044*b*, 1044*c* and occlusion members 1048*b*, 1048*c*.

Figure 25D:
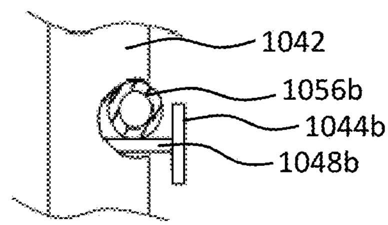
FIG. 25D shows a close-up view of an occlusion member and retention member as shown in FIG. 25B.

The retention member 44*b* (FIGS. 25B and 25D) is in a second, closed position wherein the retention member 44*b* still prevents the tubing segment 1056*b* from being withdrawn from the channel 1060 in which it is disposed. Movement of the retention member 1044*b* into the second, closed position coincides with movement of the occlusion member 1048*b* downwardly from the first, closed or occluding position discussed above regarding occlusion member 48*a*, in to a second, open position wherein the occlusion member 1048*b* is no longer pinching closed the tubing segment 1056*b*. Thus, moving the retention member 1044*b* and occlusion member 1048*b* into the second position allows fluid flow through the tubing without releasing the tubing segment 1056*b* from the tube retention unit 1042. This may be accomplished by pressing one of the buttons, such as button 1036*b* or 1038*b* (FIG. 26) to move the associated retention member 1044*b* and occlusion member 1048*b* downwardly.

The retention member 1044*c* in FIG. 25A has been moved into a third, open position. This also results in the occlusion member 1048*c* being moved into a third, open position. With the retention member 1044*c* in the third, open position, the retention member no longer prevents the tubing segment (not show) from being removed from the channel 1060. As will be discussed in additional detail below, it is preferred that movement of the retention member 1044*c* into the third, open position require some action different than what would be required to move the retention member into the second, closed position. This may require, for example using two buttons (i.e. both buttons 1038*c* and 1036*c*), or require use of button 1036*c* where a user usually uses button 038*c* to move the retention member 1044*c* between the first, closed position and the second, closed position, thereby moving the occlusion member 1048*c* between the first, closed position and the second, open position. The movement into the third, open position may also be implemented by requiring the buttons 1036 and/or 1038 to be moved substantially beyond the normal range needed for movement of the retention members 1044 and occlusion members 1048 between the first and second positions, or by require a release which allows the button to be moved into a certain position. Thus, a user will not accidentally move the retention member 1044*c* into the third, open position and allow the tubing segment to be withdrawn by simply pressing too hard on the button used to open or close flow through the tubing.

Figure 26:
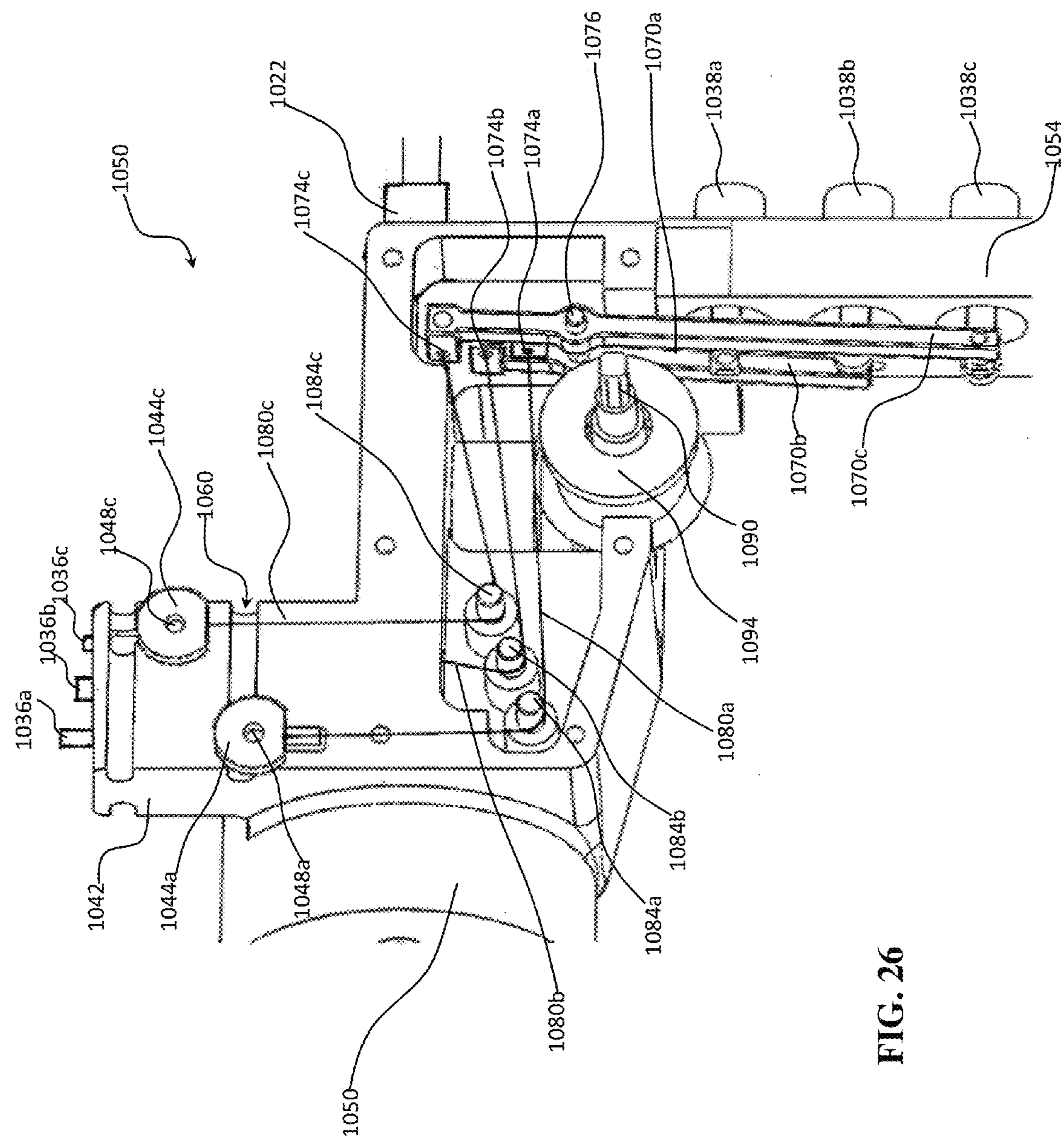
FIG. 26 shows a side, partially cut-away view of a control unit with its actuation mechanisms exposed formed according to principles of the present invention.

Now discussing generally FIGS. 25A-26, in the first, closed position the occlusion members 1048*a*-1048*c* may be biased into position at or near the roof of channels 1060 so as to pinch closed tubing, which may be passing over the occlusion members 1048*a*-1048*c*, to thereby prevent flow of fluid in either direction through the tubing segment. Tube mounting unit 1042 may include plungers, buttons, knobs, or the like, such as 1036*a*-1036*c* which may be used to overcome the force exerted by the biasing member to move the occlusion members 1048*a*-1048*c* to a load position, such as is indicated by occlusion member 1044*c* in FIG. 25A, thus allowing access to channels 1060. (While such movement is discussed above as moving from a first, closed position to a third, open position, it will be appreciated that multiple positions may be provided, or that the retention members and occlusion members may be formed which operate independently of one another. Thus, any reference to first, second, etc., positions, is for convenience and shall not be deemed to be limiting).

In use, pushing down on plunger 1036*c* (FIG. 26) may provide sufficient force to move occlusion member 1044*c* to the load position as shown in FIG. 25A. After a tubing segment is positioned in the channel 1060, plunger 1036*c* may be released and a biasing element (such as a spring, band, etc., may cause the retention member 1044*c* to return to the first, closed position to thereby hold the tubing in channel 1060 and the occlusion member 1048*a* to pinch closed the tubing. The same may be repeated for some or all of the retention members and occlusion members so that a plurality of tubing segments are removeably attached to the tube mounting unit 1042 and selectively occluded.

Controlling flow of fluid through a tubing section located in channel 1060 may be accomplished by moving the occlusion members 1048*a*-1048*c* between a plurality of positions using an actuation mechanism that may be operatively connected to the occlusion member 1044*a*-1044*c* (such as the actuation mechanism of control unit 1050 shown in FIG. 16). For example, flow of a fluid through tubing section 1056*a* may be substantially prevented by occlusion member 1048*a*, which is in a closed position, whereas fluid may easily flow through tubing section 1056*b* because occlusion member 1048*b* is in an open position.

The actuation mechanism shown in FIG. 26 may allow the user of an optical medical tube and control unit assembly 1010 to easily control the amount of fluid passing through a tubing section held in a channel 1060 by moving the occlusion members 1048*a*-1048*c* to a plurality of positions between, and including, the open and closed positions by applying force to, or removing the same force from, plungers, buttons, knobs, etc. 1038*a*-1038*c*. As can be seen in FIG. 26, the control unit 50 may include multiple buttons which can be used to perform a variety of functions while the assembly is in use, e.g. flushing, aspiration, and/or insufflation.

Buttons 1038*a*-1038*c* may be located on handle 1054 to permit a user to grip and maneuver the assembly 1010 while simultaneously performing other various functions. Actuation of the occlusion members 1048*a*-1048*c* to control flow through tubing may be accomplished using buttons 1038*a*-1038*c* and the cable and lever actuation system, as shown in FIG. 26. For example, occlusion members 1048*a*-1048*c* may be biased in a closed position (1048*a* in FIG. 25A, 25C) by including a biasing member, such as a spring, in the control unit 1050 that biases the occlusion members 1048*a*-1048*c* towards the roof of the channels 1060. It is generally advantageous to have the occlusion members 1048*a*-1048*c* biased in the closed position so that when the assembly 1010 is in use a fluid is not inadvertently introduced into or aspirated from the body. When a user of the assembly 1010 wishes to open a fluid pathway in a tubing segment that may be held in the channels 1060 of the tube mounting unit 1042, the user need only apply a force to one of the buttons or knobs 1038*a*-1038*c*. For example, pushing button 1038*a* overcomes the force exerted by a biasing member associated with occlusion member 1048*a* when the force from pushing button 1038*a* is transferred to the occlusion member 1048*a* and applied in an opposite direction than the force applied by its associated biasing member. Overcoming the force exerted by the biasing member opens a fluid pathway in a section of tubing in communication with the occlusion member 1048*a* to allow fluid to pass therethrough (see tubing 1056*b* FIG. 25B, 25D).

In further detail, the button 1038*a* may be connected to lever 1070*a* at one end, which may be pivotably attached to the control unit 50 at pivot point 76. Cable 1080*a*, which attaches to occlusion member 1048*a*, may operatively connect the button 1038*a* to the occlusion member 1048*a* via its connection to the opposite end of the lever 1070*a* at an attachment point 1074*a*. (It will be appreciated that the cables 1080*a*-1080*c* may alternatively be strings, wires, lines, strands, rods, bands, belts, straps, or the like) Depending on the orientation of the occlusion member 1048*a* on the control unit 1050 relative to the cable attachment point 1074*a* on the lever 1070*a*, cable 1080*a* may also have to be redirected using structures 1084*a*, which may be any structure that provides a fulcrum point for the cable 1080*a* to pivot around. As is shown in FIG. 10, because occlusion member 1048*a* is offset relative to the cable attachment point 1074*a*, structure 1084*a* is used as a fulcrum point so that the force generated by pushing button 38*a* is ultimately applied to the occlusion member 1048*a* in a direction substantially opposite the direction of force being exerted by a biasing member.

A fluid pathway may be opened in other channels 1060 of tube mounting connecter 1042 in similar fashion by actuation of the occlusion members 1048*b* or 1048*c*, or any number of occlusion members that may be associated with the tube mounting connecter 1042. It will be appreciated that the cable and lever system shown in FIG. 26 is intended to be exemplary of the actuation mechanisms that may be used in accordance with principles of the present invention, and that the optical tube and control unit assembly 1010 contemplated herein may utilize a variety of systems to control flow of fluid through tubing.

According to one aspect of the invention, the buttons 1038*a*-1038*c* may be used to move occlusion members 1048*a*-1048*c* from a closed, occluding position to an open, non-occluding position, but are unable in a normal use configuration to move the occlusion members sufficiently to move the retention members 1044*a*-1044*c* into an open or load position. Thus, buttons 1038*a*-1038*c* may only be used to move the occlusion members 1048*a*-1048*c* sufficiently to control flow through the tubing segments, but not to allow removal of the tubing segments from the channels. To load tubing segment to the tube mounting device 1042, retention members 1044*a*-1044*c* (and occlusion members 1044*a*-1044*c*) must be moved using a force that is applied instead of or in addition to buttons 1038*a*-1038*c*. Such separate force may be provided by pressing plungers 1036*a*-1036*c* described above. Alternatively a force may be applied directly to retention members 1044*a*-1044*c*, independent any separate structure. It will be appreciated that there are a variety of methods for applying a force to retention members 1044*a*-1044*c* consistent with principles described herein.

By requiring a separate force to move the retention members 1044*a*-1044*c* to the load position, the risk that tubing located in channel 1060 will accidently be displaced from the tube mounting unit 1042 during use of the assembly is reduced as retention members 1044*a*-1044*c* block the exit of a piece of tubing from channel 1060 even when the occlusion members 1048*a*-1048*c* are in the open position. Therefore, a user of the assembly 1010 can be confident that he or she will be able to perform a desired function at the proper time by simply pressing buttons 1038*a*-1038*c*.

Figure 27A:
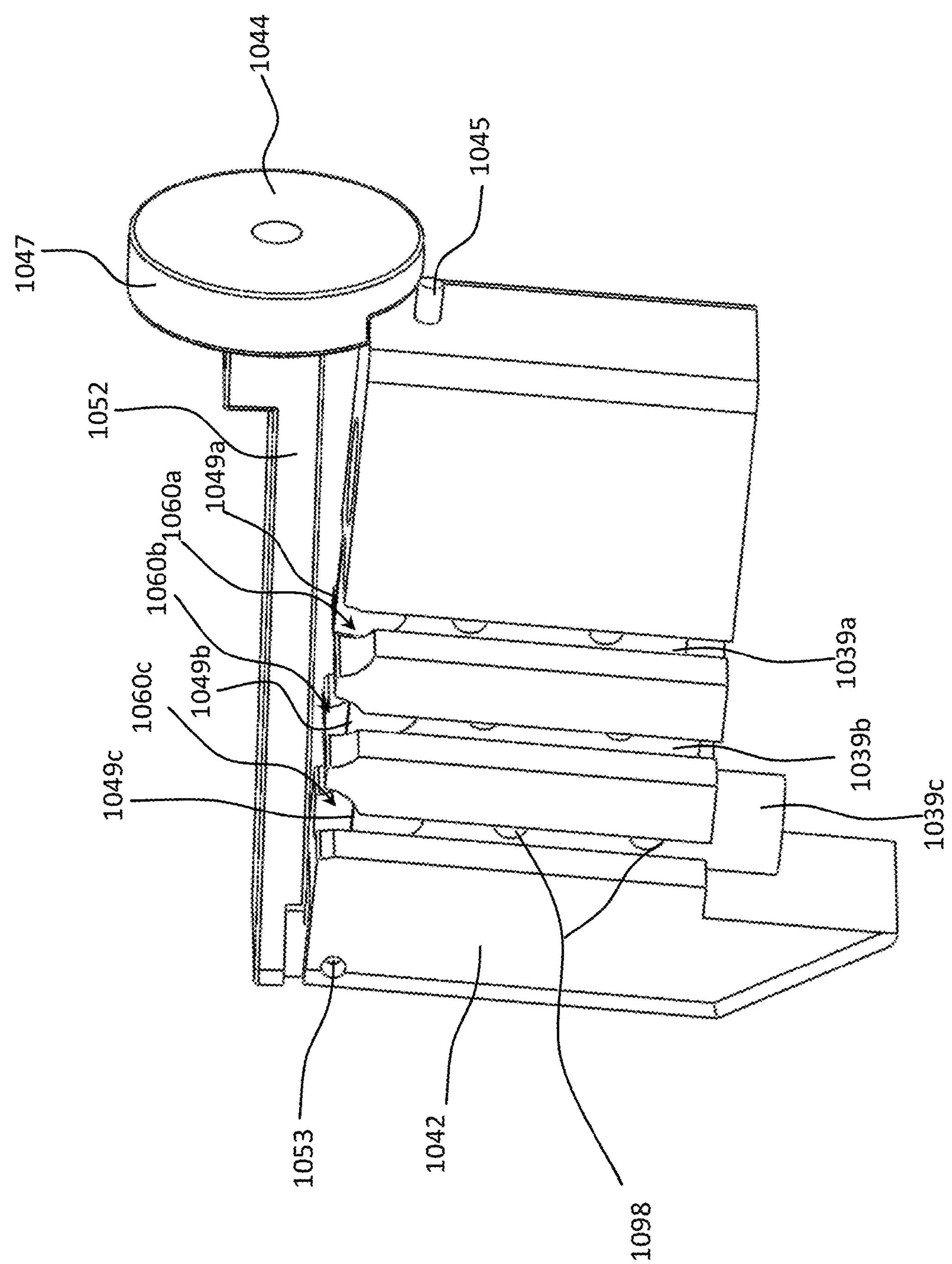
FIG. 27A shows a perspective view of another tube mounting unit according to one aspect of the present invention.
Figure 27B:
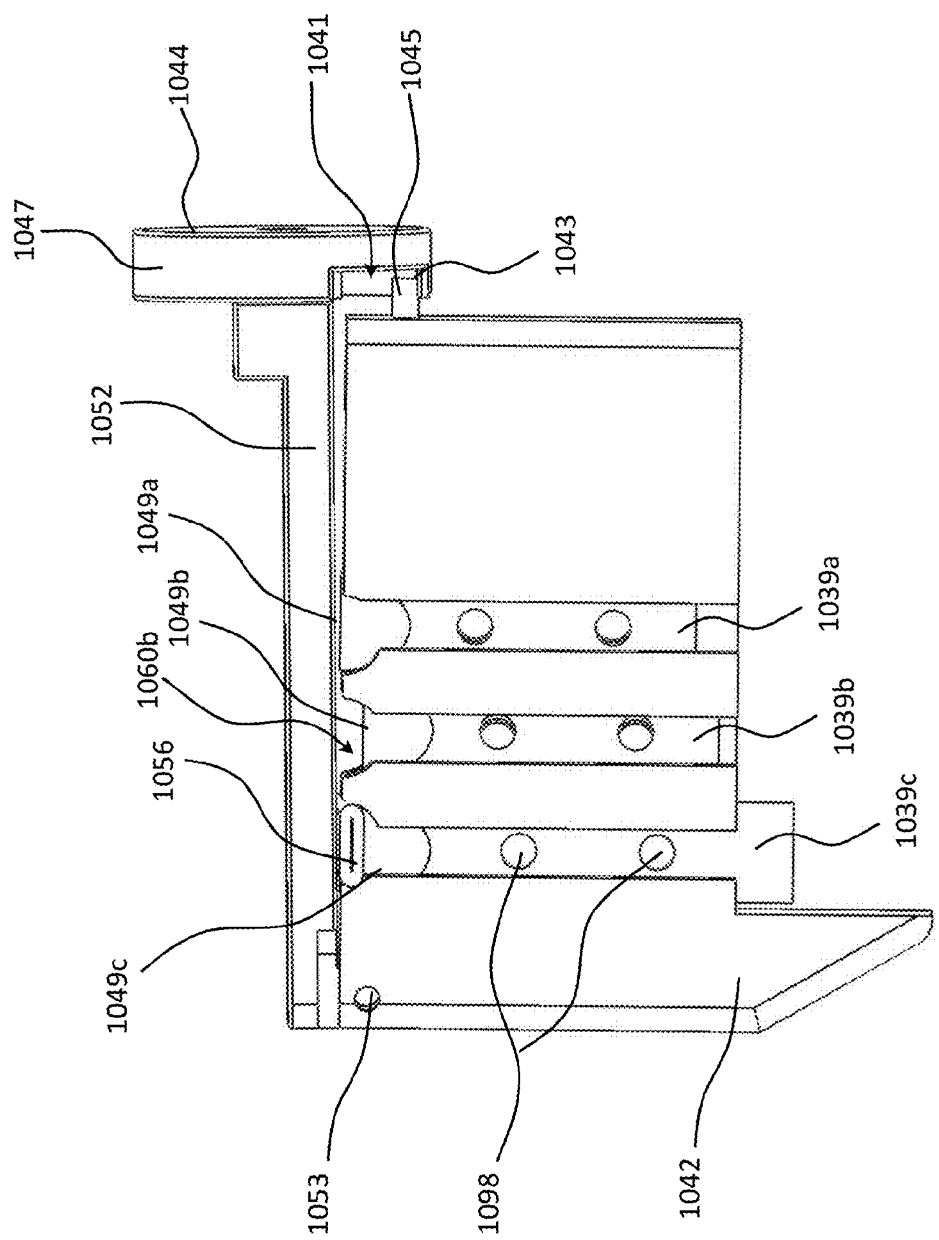
FIG. 27B shows a side view of the tube mounting unit shown in FIG. 11A with an occluded tubing segment.
Figure 27C:
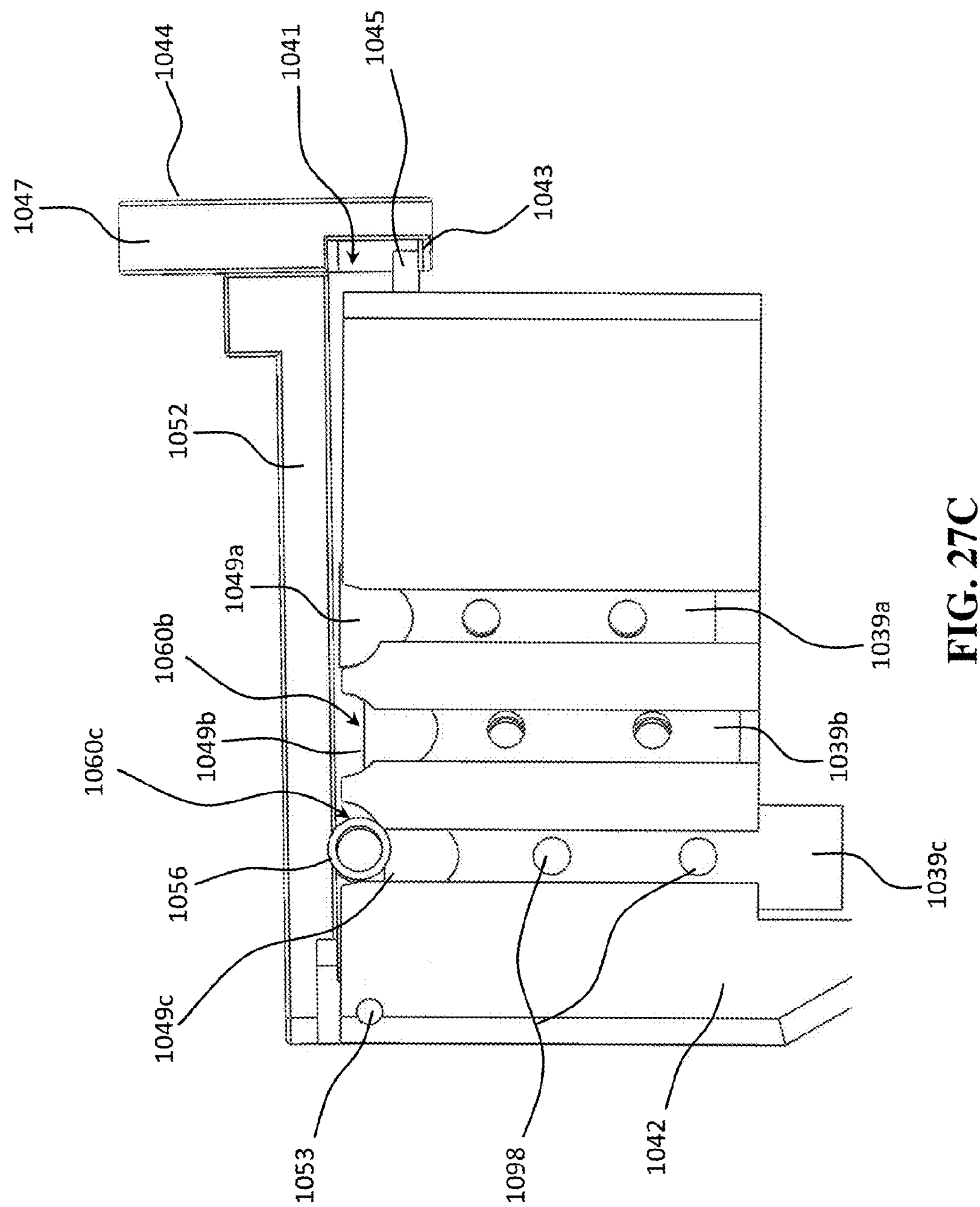
FIG. 27C shows another side view of the tube mounting unit shown in FIG. 11A.

Turning now to FIGS. 27A-27C, there is shown another tube mounting unit 1042, according to one aspect of the present invention. The tube mounting unit 1042 may comprise a body having one or more retention locations 1060, such as a space, void, channel etc. for receiving tubing sections, such as a disposable tubing section described in more detail below. The tube mounting unit 1042 may also comprise at least one retention member 1044 for holding tubing sections in the one or more retention locations 1060 of the body. The retention member 1044 may include an arm 1052 and a locking member 1045. The arm 1052 may be connected to the tube mounting unit 1042 such that the arm 1052 is located adjacent the retention locations 1060 when the retention member 1044 engages the locking member 1045. As shown in FIGS. 27A-27C the arm 1052 may be pivotably connected to the tube mounting unit 1042 at location 1053. However, it will be appreciated that the arm 1052 may connect with the tube mounting unit 1042 in other manners as well.

The tubing mounting unit 1042 may removably receive one or more tubing segments in the retention locations 1060*a*-1060*c*. The arm 1052 may be pivoted away from the tube mounting unit 1042 to allow access to the retention locations 1060*a*-1060*c*. After one or more tubing segments are position in the retention locations 1060*a*-1060*c*, the arm 1050 may be pivoted such that the retention member 1044 is in a position to engage the locking member 1045 to securely hold the one or more tubing segments in the retention locations 1060*a*-1060*c*. As shown in FIGS. 27A-27C, locking member 1045 may be a projection disposed on the tube mounting unit 1042 and the retention member 1044 may include a sidewall 1047. The retention member 1044 may releasably engage the locking member 1045 by, for example, moving the locking member 1045 through a notch or void 1041 in the sidewall 1047 and rotating the retention member 1044 such that the locking member 1045 comes into contact with an inner surface 1043 of the sidewall 1047. It will be appreciated that the retention member 1044 may releasably engage the tubing mounting unit 1042 in a number of ways such that one or more tubing sections may be securely held in the retention locations 1060*a*-1060*c*.

Also shown in FIG. 27A are a plurality of actuation members 1039*a*-1039*c* which may be disposed in channels 1041*a*-1041*c* in the tubing section 1042. The actuation member 1039*a*-1039*c* may be disposed so as to intersect the retention locations 1060*a*-1060*c* to thereby engage and selectively prevent or otherwise control flow through tubing disposed in the retention locations. The actuation members 1039*a*-1039*c* may be, for example, plungers which are biased into a first, closed position wherein they extend into the retention locations 1060*a*-1060*c*, respectively, to engage and control fluid flow through tubing segments.

In order to improve the ability of the actuation members 1039*a*-1039*c* to pinch closed tubing passing through the retention locations 1060*a*-1060*c*, an upper end 1049 of the actuation members may be tapered to a ridge so as to minimize the surface area engaging the tubing. The ridge may be disposed generally perpendicular to the length of the tubing to improve the ability to close the tubing.

Referring now more particularly to FIGS. 27B-27C, a tubing section 1056 is shown located in the retention location 1060*c* and disposed in communication with an end 1049*c* of the actuation member 1039*c* The actuation member 1039*c* may be biased towards the tubing segment 1056 (thus pinching the tubing closed) by a biasing member unless acted on by some other force. Thus as shown in FIG. 27B, the tubing section 1056 is closed and will prevent or substantially prevent flow therethrough.

A cable and lever system, such as the system described in FIG. 26 above, may engage the actuation members 1039*a*-1039*c* at one or more locations 1098 via a number of mechanisms, such as set screws to pinch and hold the cable. The cable and lever system (or other system) may be used to apply a sufficient force to the actuation member 1039*c* to overcome the force being exerted by the biasing member to thereby move the actuation member 1039*c* away from the tubing 1056 and open a fluid flow channel through the tubing as shown in FIG. 27C. It will be appreciated that the actuation member 1039*c* may be movable between a plurality of positions between the open and closed position so that the actuation member may be used to partially close the tubing and thereby regulate rate of fluid flow through the tubing in addition to simply providing for flow and no flow configurations.

It will be appreciated that a fluid pathway may be opened in other tubing segments located in retention locations 1060*a* and 1060*b* in similar fashion, or any number of retention locations that may be associated with the tube mounting unit 1042.

Figure 28:
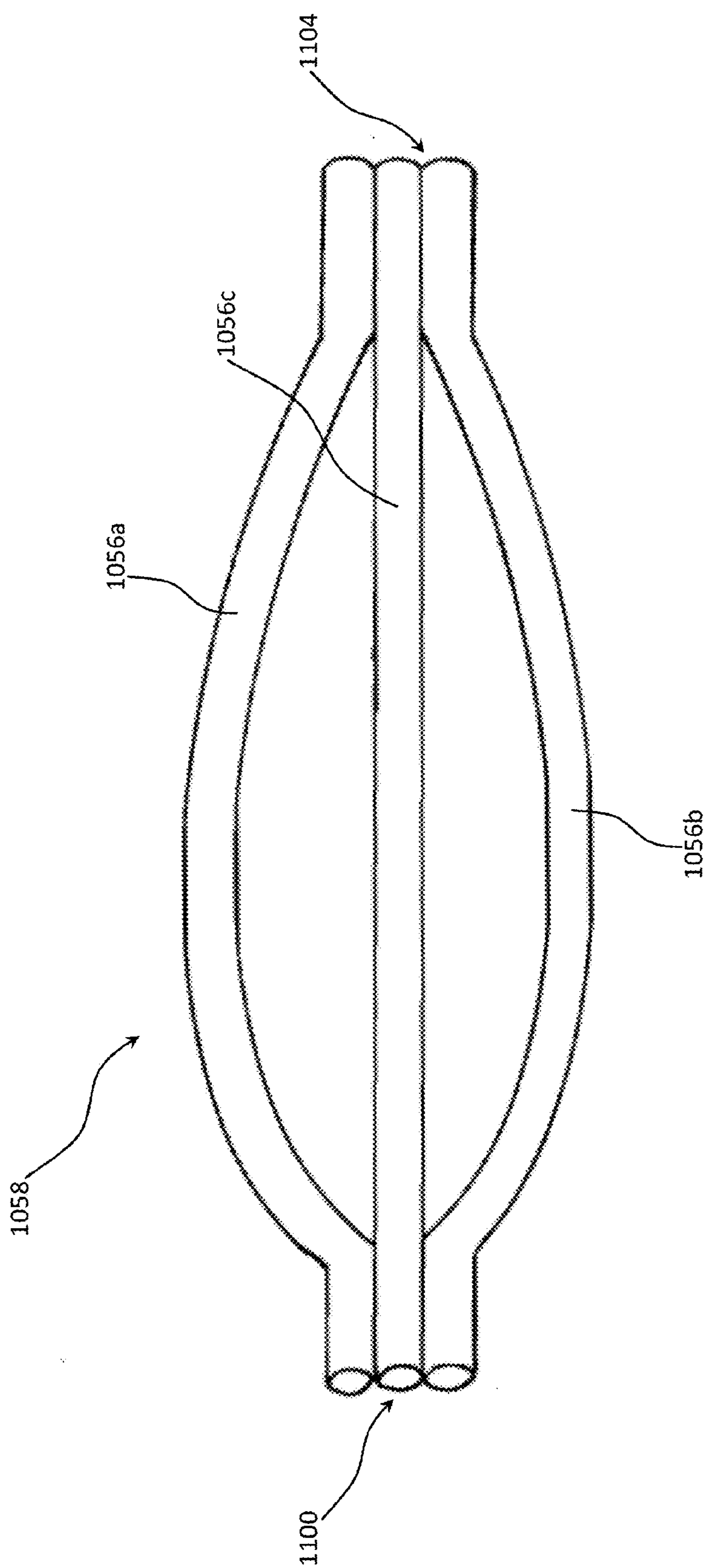
FIG. 28 shows a side view of a tubing section made in accordance with principles of the present invention.

Turning now to FIG. 28, there is shown a side view of a tubing section, generally indicated at 1058, made in accordance with one aspect of the present invention. The tubing section 1058 may have multiple tube sections 1056*a*-1056*c* each of which may be received by a retention location 1060, such as a channel (See e.g. FIG. 25A) or a space, void, etc. (See e.g. FIG. 27A) 1060 in the tube mounting unit 1042. The multiple tube segments 1056*a*-1056*c* of the tubing section 1058 may be connected together at ends 1100 and 1104 and separated into individual tube sections between ends 1100 and 1104 to thereby facilitate mounting of the tubing section 1058 to tube mounting unit 1042.

End 1100 of the tubing section 1058 may be configured for quick and easy coupling to a tube adaptor (not shown) of the present invention. Additionally, the end 1104 may be configured for quick and easy coupling to devices designed to deliver fluid or air, or provide suction, to thereby operatively connect medical tubing 30 (FIG. 17) to such devices via the tubing section 1058. After use the tubing section may be discarded. Thus, unlike an endoscope which typically has lumens for flush, aspiration, and insufflation embedded in its handle making it a requirement that the endoscope go through a preparation and sterilization process prior to reuse, the control unit assembly 1050 may be reused almost immediately after it is removably disconnected from a medical tube 1030 because it does not come into contact with body fluids, etc. It will be appreciated that a single control unit 1050 may be used to place medical tubes 1030 in multiple patients, and/or reconfirm that a medical tube 1030 remains in its proper location in the body in multiple patients, over a short period of time.

It will also be appreciated that tubing section 1058 shown in FIG. 28 is only one example of a tubing section that may be used with the assembly 1010 according to principles of the present invention. Other examples of appropriate tubing sections that may be loaded on the tube mounting unit 1042 may include tubing sections having more or less tubes, or tubing sections whose tubes are not connected or only connected at one end. Also, the tubes associated with a tube adaptor 1020 may directly load on to the tube mounting unit 1042. These examples, though not exhaustive, illustrate the present inventions advantage over traditional endoscopes, namely that the tubing section and the control unit of the assembly can be readily disassociated from each other in order to allow the control unit 1050 to be removably connected to a different medical tube 1030 in a short amount of time and without the need for repeated sterilization.

Figure 29A:
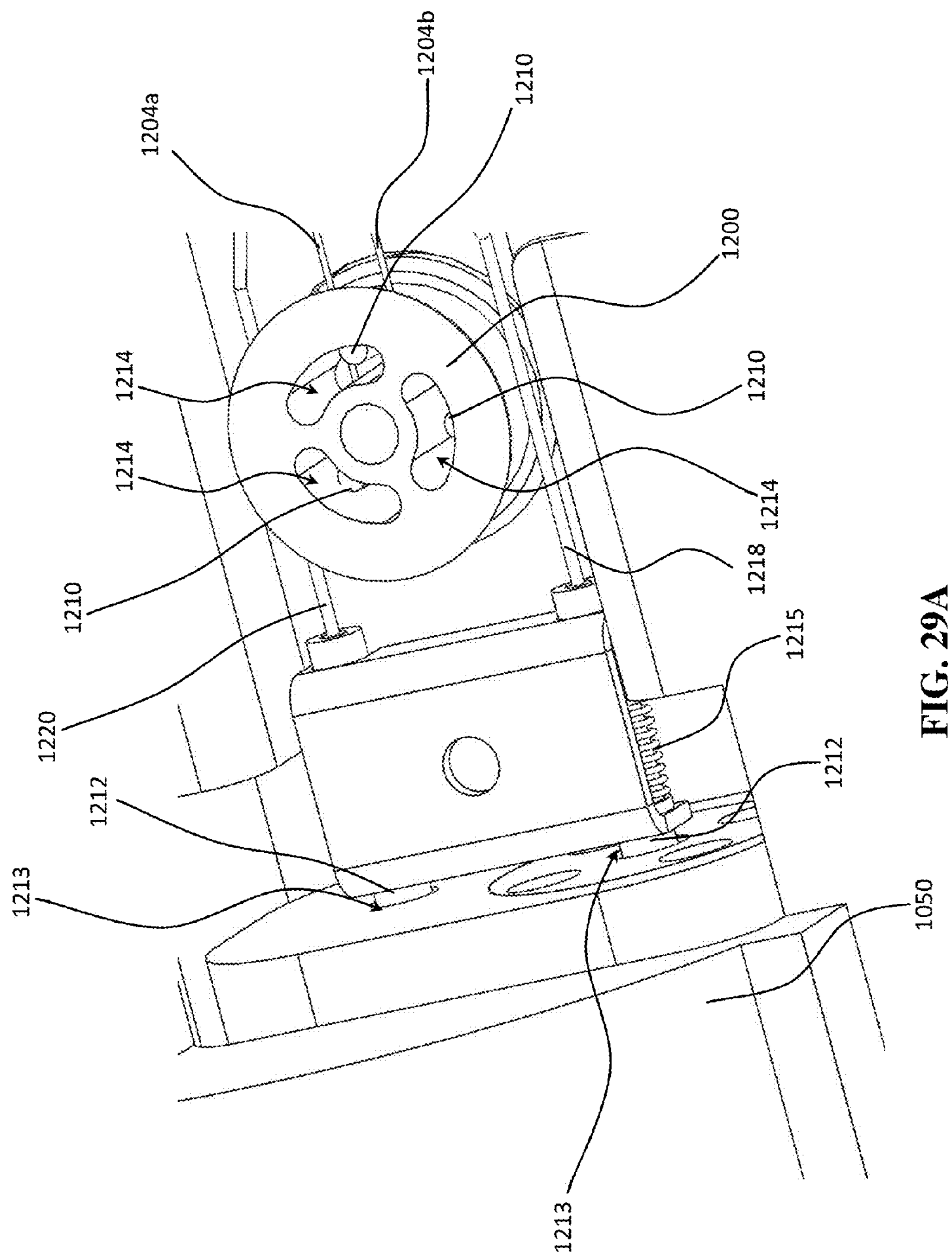
FIG. 29A shows a fragmented, close-up top view of a steering mechanism having a wheel coupled to a control unit of an optical tube and control unit assembly of the present invention.
Figure 29B:
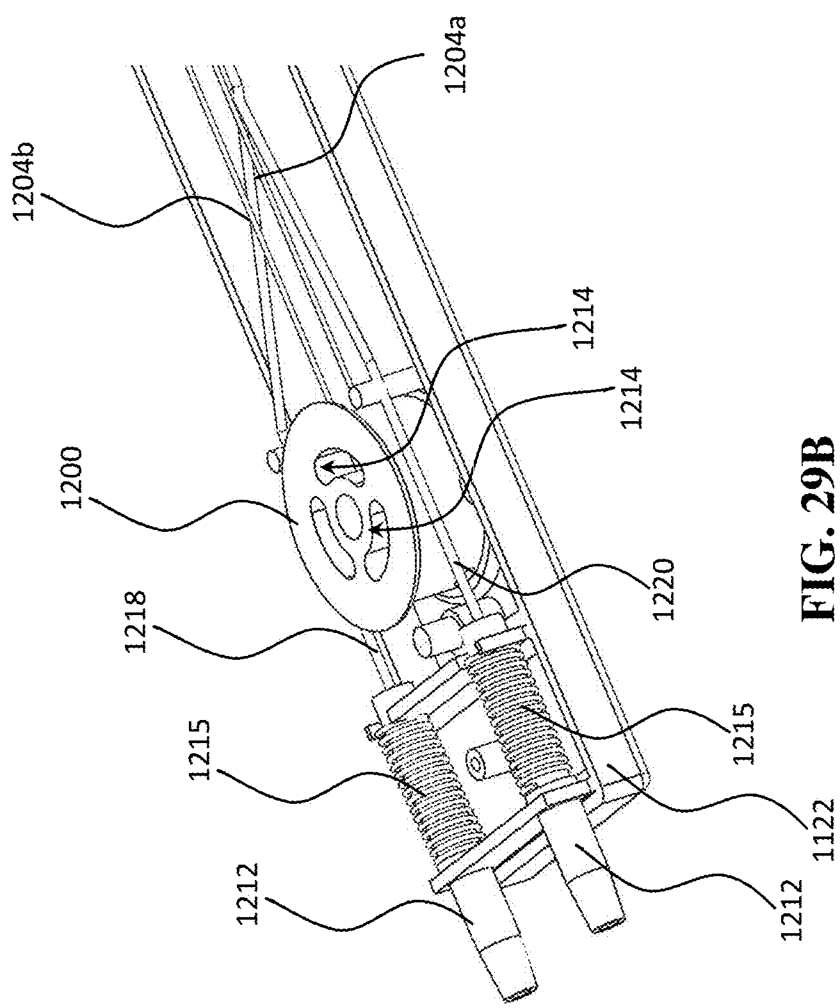
FIG. 29B shows a fragmented, perspective view of a coupling adaptor for connecting the optics and steering mechanism of an optical medical tube with a control unit assembly.

Now turning to FIGS. 29A and 29B which show exemplary mechanisms for coupling the optics and steering mechanism of an optical medical tube with a control unit assembly according to principles of the present invention. As can be seen in FIG. 29A, a steering mechanism having a pivotable member 1200, such as a wheel, may be easily and quickly coupled to a control unit 1050 of an optical tube and control unit assembly 1010 of the present invention. The steering mechanism may be incorporated in the coupling adaptor 1022 and may be made very small, e.g. about 0.5 inches in diameter, so that it provides little weight and bulk at the end of the medical tube 1030.

The steering mechanism may facilitate navigation of a tube 1030 (see FIG. 17) through a tortuous pathway. The steering mechanism may include multiple steering wires 1204*a* and 1204*b* that are wrapped around the wheel 1200. (Although not shown, it should be apparent from the above discussion that the steering wires 1204*a* and 1204*b* are associated with an optical medical tube of the present invention.) Steering wire 1204*a* may wrap around the wheel 1200 in a counterclockwise direction and steering wire 1204*b* may wrap around the wheel 1200 in a clockwise direction wire 1204*a* so as to provide for multidirectional movement of an optical medical tube of the present invention. For example rotation of the wheel 1200 in a clockwise fashion will result in steering wire 1204*b* being pulled towards the control unit 1050 and provide additional slack to steering wire 1204*a*, thus ultimately resulting in an associated optical medical tube being deflected in the direction of steering wire 1204*b*. It will be appreciated that the associated optical medical tube may be deflected in the opposite direction by rotating the wheel in a counterclockwise fashion. It will also be appreciated that more or less wires may be included in an optical tube and control unit assembly of the present invention, which in turn may provide a user of such an assembly with more or less control over the movement of an optical medical tube.

One advantage of the engagement of the steering wires 1204*a* and 1204*b* and the wheel 1200 is that the wires can be controlled in a very compact space. This allows the wheel and wires to be kept with the medical tube if desired.

The wheel 1200 may be coupled to the control unit 1050 via one or more slots 1214 in wheel 1200 and one or more pins 1210 located on the control unit 1050. (Of course, the configuration could also be reversed with the pin(s) being located on the wheel 1200 and the slot(s) being on the control unit 1050). Such a configuration for coupling the wheel 1200 to the control unit 50 provides for quick and easy connecting of the steering wires 1204*a* and 1204*b* so that a user may control movement of an optical medical tube via the control unit 1050.

It will be appreciated that other steering mechanisms may be used, such as, for example, a bar which pivots and has the steering wires 1204*a* and 1204*b* attached to opposing ends. The wheel configuration is believed to be advantageous as the wheel can be made to undergo multiple rotations if necessary, thus allowing the wheel to be very small in relative size.

Referring back to FIG. 26, a control unit 1050 may include a gear system 1094 which is operatively connected to the pins 1210 in FIG. 29A. Gear system 1094 may include a drive 1090 which, when rotated, actuates gear system 1094 thereby moving pins 1210 and turning wheel 1200 in a clockwise or counterclockwise direction depending on which way drive 1090 is rotated. Drive 1090 may be configured to receive a drive member, such as thumbwheel 1026 (FIG. 17) so that a user of assembly 1010 may easily rotate drive 1090 to steer an optical medical 1030 tube of the present invention. It will be appreciated that a steering mechanism comprised of a gear system 1094 is exemplary of the steering mechanisms of the present invention and that alternative steering mechanisms may be contemplated.

FIG. 29A also shows mounting structures 1212, such as ferules, associated with coupling adaptor 1022 which may be inserted into openings 1213 on control unit 1050. The mounting structures 1212 surround the ends of the optical wires 1218, 1220 and provide support thereto as the optical wires 1218, 1220 are brought into contact with the optical system (e.g. image capturing device and/or light source) disposed in the control unit 1050.

The mounting structures 1212 may include or be disposed in communication with biasing members 1215, such as a springs, elastomeric material, etc., which may facilitate alignment and seating of each mounting structure 1212 to a specified depth for substantially optimum interaction of the imaging device 134 (not shown) located in tube 1030 with an image capturing device and/or light source located in the control unit 1050. Alignment and seating of the posts 10212 to the specified depth within openings 10213 may provide for quick, high quality visual data while reducing the need for manual focusing and alignment with elements in the housing 1046 (FIG. 30).

It will be appreciated that the coupling adaptor 1022 may be removed from the control unit 1050 after initial placement of the feeding tube 1030. In order to allow a physician or other medical personnel to quickly verify that the distal end of the feeding tube 1030 is in the proper location, it is advantageous that the coupling adapter 1022 quickly and easily nest in the control unit. This may be accomplished by sliding the mounting structures 1212 into the openings 1213 and the control unit and pushing the coupling adapter 1022 down so that the projections 1210 engage the openings 1214 of the wheel 1200.

Figure 30:
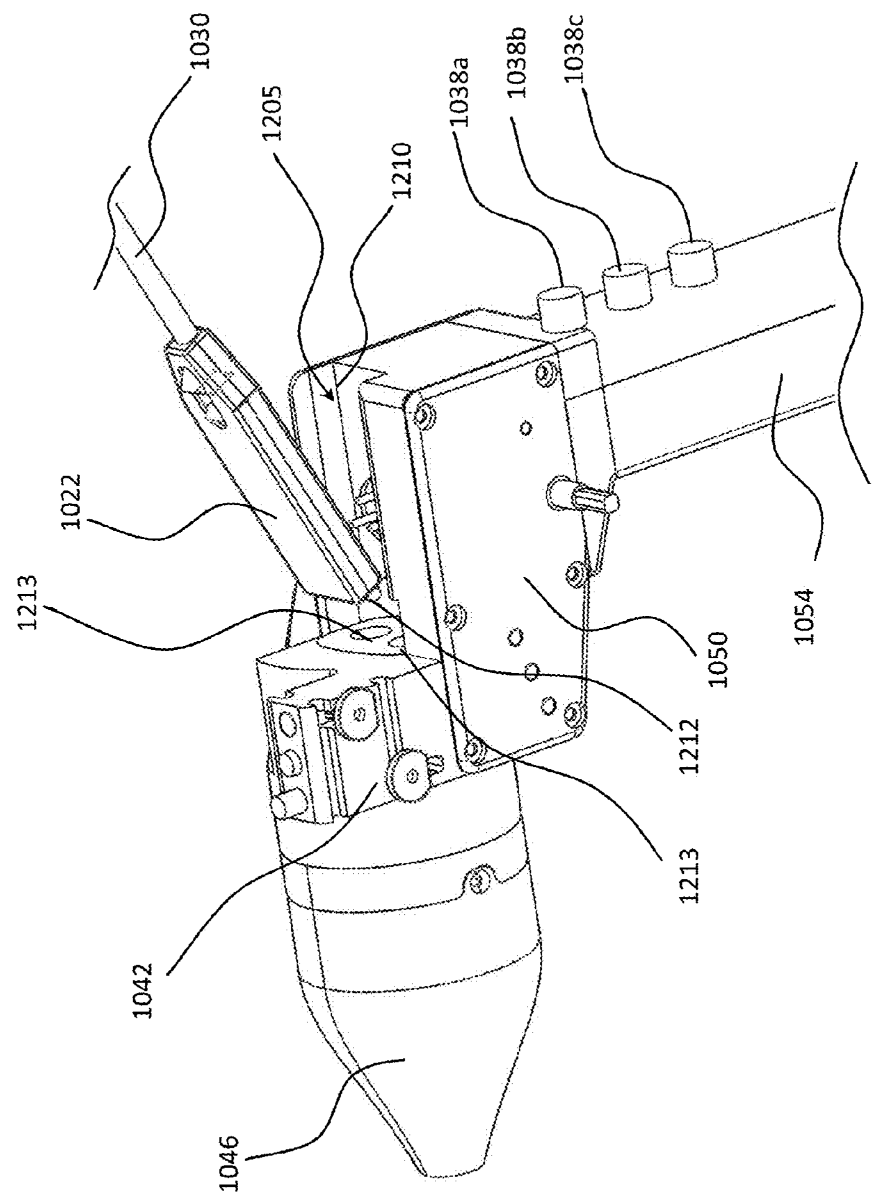
FIG. 30 shows a fragmented, perspective view of a coupling adaptor being removably connected to a control unit according to principles of the present invention.

Turning now to FIG. 30, there is shown a fragmented, perspective view of a coupling adaptor 1022 being removably connected to a control unit 1050 according to principles of the present invention. Coupling adaptor 1022 may comprise a wheel 1200 of the steering mechanism described above positioned so as to couple with a steering engagement member, such as pins 1210 on control unit 1050 when coupling adaptor 1022 is seated in a recess 1205. As discussed above the coupling adaptor 1022 may include mounting structures 1212, such as posts of ferules, having a biasing member (not shown) which are intended to be insert into opening 1213 on control unit 1050 and which may facilitate alignment and seating of the biased mounting structure 1212 (and the end of the optic wires 1204*a* and 1204*b* to a specific depth. Additionally, openings 1213 may be chamfered in order to further facilitate alignment of the various components of an optical medical tube 1030 and the control unit 1050 when coupling adaptor 1022 is seated in recess 1205. The control unit 1050 can be used to control visualization, flow of fluids into or out of the tube 1030, and steering when the coupling adaptor 1022 is attached, and then be removed whenever convenient.

Figure 31:
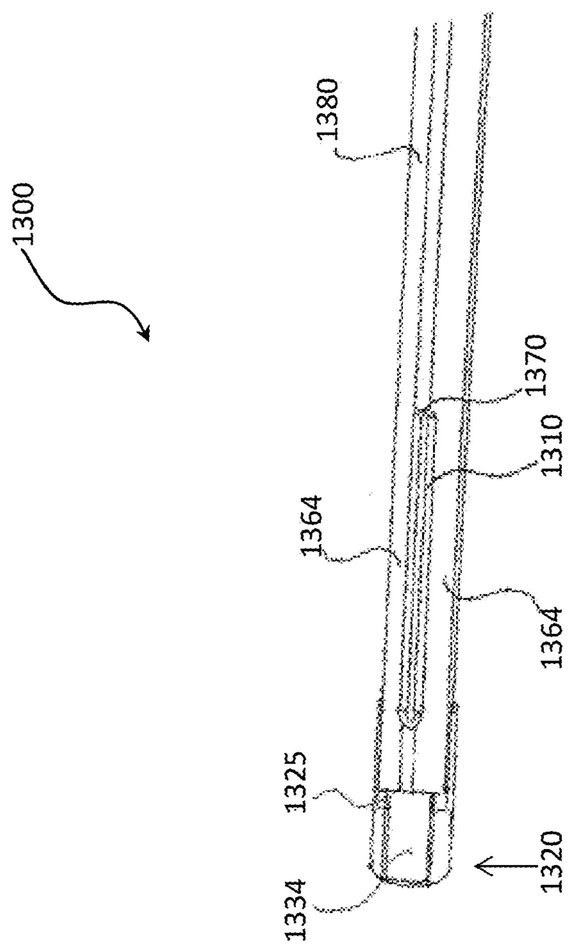
FIG. 31 shows a perspective, cutaway view of a stylet and tube tip of a medical tube according to principles of the present invention.

FIG. 31 shows a perspective, cutaway view of a stylet 1380 and tube tip 1320 at the distal end of a medical tube, generally indicated at 1300. The stylet 1380 is generally similar to the stylet 1280 referred to in FIG. 23B. One aspect of the present invention that is more readily seen in FIG. 31 is the tube tip 1320. The tube tip 1320 is attached to the tube 1300 so that there is a standoff or gap 1325 between the tip 1320 and the distal end of the stylet 1380. The gap 1325 may facilitate flushing, aspiration, and/or insufflation by ensuring that sufficient space exists between the tube tip 1320 and one or more lumens in the stylet 1380. Likewise, the gap 1325 may facilitate flow of medication or nutrients from lumens 1334 past the tube tip 1320.

Also shown in FIG. 31 is a cutaway 1364 in the stylet 1380. The cutaway 1364 is formed by removing a portion of stylet 1380 at the distal end of the tube 1300. It will be appreciated that the stylet 1380 may include one or more cutaways 1364 and that the one or more cutaways 1364 may provide increased deflection at the distal tip of the tube 1300, thus allowing the tube 1300 to be more easily advanced through complex and tortuous pathways. The generally X-shaped extrusion profile of the stylet 1380 in conjunction with one or more cutaways 1364 may allow for tubes with steering capabilities that are less expensive to manufacture than tubes made with multiple durometers of materials attached end to end to obtain similar steering capabilities.

Additionally, steering member (not shown) may be disposed in communication with the stylet For example, steering wires may pass through the lumen 1370 and attach at tube tip 1320, or at some other location near the distal end of the medical tube 1300. Thus, pulling a steering wire in a direction away from the distal end of the medical tube will deflect the distal end away from the center axis of the tube 1300. One skilled in the art will appreciate that the cutaway 1364 may allow the distal end to be deflected upon less force being used to pull a steering wire and/or exaggerate the amount the distal end of the tube 1300 is deflected.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention. Additionally, all structural and functional equivalents to the elements of the various embodiments described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

There is thus disclosed an improved optically guided medical tube and control unit assembly and methods of using the same that reduces risks associated with the placement of medical tubes inside the body of a patient and may be used to reconfirm proper placement after the medical tube has been associated with the patient for an extended period of time.

What is claimed is:

1. An optical tube and control unit assembly comprising:

a control unit comprising a tube mounting unit and a steering mechanism; and an optical tube assembly selectively attachable and detachable from the control unit, the optical tube assembly comprising:

a tube;

at least one steering member disposed at least partially in the tube of the optical tube assembly;

an imaging device disposed at least partially in the tube of the optical tube assembly; and a stylet for receiving the at least one steering member and the imaging device;

wherein the stylet is removably disposed in the tube of the optical tube assembly, and the steering mechanism selectively controls the at least one steering member when the optical tube assembly is attached to the control unit.

2. The optical tube and control unit assembly of claim 1, wherein the optical tube assembly further comprises a coupling adaptor, and wherein the optical tube assembly is removably connected to the control unit via the coupling adaptor.

3. The optical tube and control unit assembly of claim 2, wherein the optical tube assembly further comprises a pivotable member disposed on the coupling adaptor for engaging the control unit's steering mechanism.

4. The optical tube and control unit assembly of claim 2, wherein the coupling adaptor is releasably attached to the tube.

5. A method of placing a medical tube comprising the steps of:

selecting an optical medical tube assembly comprising a tube, at least one steering wire, an imaging device, and a stylet having at least a portion of the imaging device disposed therein;

attaching the optical medical tube assembly to a control unit comprising a steering mechanism;

attaching the optical medical tube assembly to a tubing section removably secured in a tube mounting unit; and advancing the optical medical tube while selectively actuating the tube mounting unit to control the flow of fluid into and out of the medical tube; and removing the stylet after placement of the tube.

6. The method according to claim 5, wherein the optical medical tube assembly has a coupling adaptor attached thereto, the coupling adaptor comprising a steering member disposed in communication with the at least one steering wire, and wherein the method comprises using the control unit to move the steering member and thereby move the at least one steering wire.

7. The method according to claim 6, wherein the steering member comprises a wheel and wherein the method comprises using the control unit to rotate the wheel.

8. The method according to claim 5, wherein the optical medical tube assembly has a coupling adaptor having a mounting structure disposed in communication with the imaging device, and wherein the method comprises attaching the coupling adaptor to the control unit such that the imaging device engages an image capturing device disposed at least partially in the control unit.

9. The method according to claim 5, wherein the optical medical tube assembly comprises a coupling adaptor, and wherein the method comprises disconnecting the coupling adaptor from the control unit following placement of the tube.

10. The method according to claim 5, wherein the optical medical tube assembly comprises a coupling adaptor and wherein the method comprises disconnecting the coupling adaptor from the tube following placement of the tube.

11. An optical tube and control unit assembly comprising:

a control unit comprising a tube mounting unit and a steering mechanism; and an optical tube assembly selectively attachable and detachable from the control unit, the optical tube assembly comprising:

a tube;

at least one steering member disposed at least partially in the tube of the optical tube assembly;

an imaging device disposed at least partially in the tube of the optical tube assembly;

a coupling adaptor for removably connecting the optical tube assembly to the control unit; and a pivotable member disposed on the coupling adaptor for engaging the control unit's steering mechanism;

wherein the steering mechanism selectively controls the at least one steering member when the optical tube assembly is attached to the control unit.

12. The optical tube and control unit assembly of claim 11, wherein the optical tube assembly further comprises a coupling adaptor, and wherein the optical tube assembly is removably connected to the control unit via the coupling adaptor.

13. The optical tube and control unit assembly of claim 12, wherein the optical tube assembly further comprises a pivotable member disposed on the coupling adaptor for engaging the control unit's steering mechanism.

14. The optical tube and control unit assembly of claim 12, wherein the coupling adaptor is releasably attached to the tube.

15. The optical tube and control unit of claim 11, wherein the optical tube assembly further comprises a stylet for receiving the at least one steering member and the imaging device, and wherein the stylet is removably disposed in the tube of the optical tube assembly.

* * * * *